US007262026B2

(12) United States Patent  
Ueno

(10) Patent No.: US 7,262,026 B2  
(45) Date of Patent: Aug. 28, 2007

(54) HEMATOPOIETIC STEM CELL PROLIFERATION REGULATORS AND POLYNUCLEOTIDES ENCODING THE SAME

(75) Inventor: Hiroo Ueno, Tokyo (JP)

(73) Assignees: Japan Science and Technology Agency, Saitama (JP); Japan as represented by the President of the National Cancer Center, Tokyo (JP)

( * ) Notice: Subject to any disclaimer, the term of this patent is extended or adjusted under 35 U.S.C. 154(b) by 87 days.

(21) Appl. No.: 10/487,421

(22) PCT Filed: Aug. 22, 2002

(86) PCT No.: PCT/JP02/08456

§ 371 (c)(1),  
(2), (4) Date: Feb. 23, 2004

(87) PCT Pub. No.: WO03/018805

PCT Pub. Date: Mar. 6, 2003

(65) Prior Publication Data

US 2004/0214189 A1  Oct. 28, 2004

(30) Foreign Application Priority Data

Aug. 23, 2001 (JP) .............................. 2001-253600

(51) Int. Cl.
| | |
|---|---|
| C12P 21/02 | (2006.01) |
| C12N 1/21 | (2006.01) |
| C12N 1/19 | (2006.01) |
| C12N 15/63 | (2006.01) |
| C12N 5/10 | (2006.01) |
| C07H 21/04 | (2006.01) |

(52) U.S. Cl. ............. 435/69.1; 435/252.3; 435/254.11; 435/320.1; 435/325; 536/23.5

(58) Field of Classification Search ..................... None  
See application file for complete search history.

(56) References Cited

FOREIGN PATENT DOCUMENTS

| WO | WO-00/42170 A1 | 7/2000 |
|---|---|---|
| WO | WO-01/32873 A1 | 5/2001 |
| WO | WO-01/40466 A2 | 6/2001 |
| WO | WO-01/46418 A1 | 6/2001 |
| WO | WO-01/49728 A2 | 7/2001 |
| WO | WO-01/53312 A1 | 7/2001 |
| WO | WO-01/53500 A1 | 7/2001 |
| WO | WO-01/66720 A1 | 9/2001 |
| WO | WO-01/68848 A2 | 9/2001 |
| WO | WO-02/10217 A2 | 2/2002 |

OTHER PUBLICATIONS

English Translation of the International Preliminary Examination Report (Dated Jun. 24, 2004.)

Supplementary European Search Report for the Application No. EP 02 76 0698, dated Oct. 12, 2005.

Database Geneseq 'Online!, "Stem cell growth factor-like polypeptide", XP002344877, Database Accession No. AAB85394, 2001, pp. 1-2 (Sep. 2001).

Database EMBL 'Online!, "Mus musculus adult male lung cDNA", XP002344878, Database Accession No. Q9DC11, pp. 1-2 (Jun. 2001).

Carninci, P. et al., "Normalization and Subtraction of Cap-Trapper-Selected cDNAs to Prepare Full-Length cDNA Libraries for Rapid Discovery of New Genes", Genome Research, Cold Spring Harbor Laboratory Press, United States, vol. 10, pp. 1617-1630 (2000).

Kawai, J. et al., "Functional annotation of a full-length mouse cDNA collection", Nature Macmillan Journals Ltd., London, Great Britain, vol. 409, 2001, pp. 685-690 (Feb. 2001).

Database EMBL 'Online!, "Tumor endothelial marker 7-related precursor: Plxdc2, Tem7R", XP002344879, Database Accession No. Q91ZV6, p. 1 (Dec. 2001).

Carson-Walter, E. B. et al., "Cell Surface Tumor Endothelial Markers Are Conserved in Mice and Humans", Cancer Research, United States, vol. 61, pp. 6649-6655 (Sep. 2001).

Teixido, J. et al., "Role of $\beta_1$ and $\beta_2$ Integrins in the Adhesion of Human $CD34^{nl}$ stem Cells to Bone Marrow Stroma", Journal of Clinical Investigation, New York, United States, vol. 90, pp. 358-367 (Aug. 1992).

Simmons, P. J. et al., "Vascular Cell Adhesion Molecule-1 Expressed by Bone Marrow Stromal Cells Mediates the Binding of Hematopoietic Progenitor Cells", Blood, W.B. Saunders, Philadelphia, VA, United States, vol. 80, pp. 388-395, (Jul. 1992).

European Search Report, Mar. 31, 2006.

Database EMBL [Online] Mar. 1, 2002 , "Sequence 585 from Patent WO0168848." XP002356794 retrieved from EBI Accession No. EM_PRO:AX376518 Database Accession No. AX376518 * the whole document*.

Database EMBL [Online] May 10, 2001, "Homo sapiens mRNA for KIAA1867 protein, partial cds." XP002356795 retrieved from EBI accession No. EM_PRO:AB058770 Database accession No. AB058770 * the whole document*.

Database EMBL [Online] Feb. 8, 2001, "Mus musculus adult male cerebellum cDNA, RIKEN full-length enriched library, clone: 1500010020 product:kin of IRRE like 3 (Drosophila), full insert sequence." XP002356796 retrieved from EBI accession No. :EM_PRO:AK005197 Database accession No. AK005197 * the whole document*.

Database EPO Proteins [Online] Feb. 13, 2002, Sequence 31 from Patent W00200691. XP002356797 retrieved from EBI accession No. EPOP:AX359727 Database accession No. AX359727 * the whole document*.

(Continued)

Primary Examiner—Robert A. Wax  
(74) Attorney, Agent, or Firm—Rader, Fishman & Grauer PLLC

(57) ABSTRACT

By analyzing hematopoietic stem cell proliferation regulators produced by stroma cells, a cDNA library is constructed and novel hematopoiesis-associated genes are isolated. Genes encoding the proteins as specified in the following (a) or (b): (a) having an amino acid sequence represented by one of SEQ ID NOS selected from the group consisting of SEQ ID NOS: 2, 4, 6, 8, 10 and 12; or (b) having an amino acid sequence derived from the amino acid sequence as defined in the above (a) by deletion, substitution or addition of one to several amino acids and having an activity of regulation hematopoietic stem cell proliferation.

10 Claims, 24 Drawing Sheets

OTHER PUBLICATIONS

Database EPO Proteins [Online] Feb. 13, 2002, "Sequence 2 from Patent W00200691." XP002356798 retrived from EBI accession No. EPOP:AX359698 Database accession No. AX359698 * the whole document*.

Database Geneseq [Online] May 2, 2001, "Human hlSLR protein sequence." XP002356799 retrieved from EBI accession No. GSN:AAB69186 Database accession No. AAB69186 * the whole document*.

Database Geneseq [Online] Mar. 9, 2001, "Human pancreatic cancer antigen protein sequence SEQ ID No:828." XP002356800 retrieved from EBI accession No. GSN:AAB54376 Database accession No. AAB54376 * the whole document*.

Database Geneseq [Online] Dec. 18, 2001, "Human DNA encoding PRO polypeptide sequence #293." XP002356793 retrieved from EBI accession No. GSN:AAS46217 Database accession No. AAS46217 * the whole document*.

International Search Report (English Translation).

Gibson et al., "Haemopoietic Growth Factor Production by Normal and Aplastic Anaemia Stroma in Long-Term Bone Marrow Culture," British Journal of Haematology, vol. 91, pp. 551-561, Blackwell Science (1995).

Varnum-Finney et al., The Notch-Ligand, Jagged-1, Influences the Development of Primative Hematopoietic Precursor Cells, Blood, vol. 91, No. 11, pp. 4084-4091 (1998).

Nagasawa et al., "Human and Mouse ISLR (Immunoglobulin Superfamily Containing Leucine-Rich Repeat) Genes: Genomic Structure and Tissue Expression," Genomics, vol. 61, pp. 37-43, Academic Press (1999).

Figure 1

SDHF-1

|MARFRRADLAAAGVMLLCHFLTDRFQFAHG|EPGHHTNDWIYEVTNAFPWNEEGVEVDSQAY
NHRWKRNVDPFKAVDTNRASMGQASPESKGFTDLLLDDGQDNNTQIEEDTDHNYYISRIYGPA
DSASRDLWVNIDQMEKDKVKIHGILSNTHRQAARVNLSFDFPFYGHFLNEVTVATGGFIYTGEV
VHRMLTATQYIAPLMANFDPSVSRNSTVRYFDNGTALVVQWDHVHLQDNYNLGSFTFQATLL
MDGRIIFGYKEIPVLVTQISSTNHPVKVGLSDAFVVVHRIQQIPNVRRRTIYEYHRVELQMSKITN
ISAVEMTPLPTCLQFNGCGPCVSSQIGFNCSWCSKLQRCSSGFDRHRQDWVDSGCPEEVQSKEK
MCEKTEPGETSQTTTTSHTTTMQFRVLTTTRRAVTSQMPTSLPTEDDTKIALHLKDSGASTDDS
AAEKKGGTLHAGLIVGILILVLIIAAAILVTVYMYHHPTSAASIFFIERRPSRWPAMKFRRGSGHP
AYAEVEPVGEKEGFIVSEQC

Figure 2

SDHF-2

|MELLSRVLLWKLLLLQSSAVLSS|GPSGTAAASSSLVSESVVSLAAGTQAVLRCQSPRMVWTQD
RLHDRQRVVHWDLSGGPGSQRRRLVDMYSAGEQRVYEPRDRDRLLLSPSAFHDGNFSLLIRAV
DRGDEGVYTCNLHHHYCHLDESLAVRLEVTEDPLLSRAYWDGEKEVLVVAHGAPALMTCINR
AHVWTDRHLEEAQQVVHWDRQLPGVSHDRADRLLDLYASGERRAYGPPFLRDRVSVNTNAF
ARGDFSLRIDELERADEGIYSCHLHHHYCGLHERRVFHLQVTEPAFEPPARASPGNGSHSSAPS
PDPTLTRGHSIINVIVPEDHTHFFQQLGYVLATLLLFILLLITVVLATRYRHSGGCKTSDKKAGKS
KGKDVNMVEFAVATRDQAPYRTEDIQLDYKNNILKERAELAHSPLPAKDVDLDKEFRKEYCK

Figure 3

SDHF-3

MRLGAAWALLLAAALGLGTRG VRAAVALADFYPFGTKRGDTVTPKQDDGGSGLQPLSVPFPF
FGAEHSGLYVNNNGIISFLKEVSQFTPVAFPIAKDRCVVAVFWADVDNRRAGDVYYREATDPA
MLNRATEDIRRYFPELPDFSATWVFVATWYRVTFFGGSSSSPVNTFQTVLITDGRFSFTIFNYESI
LWTTGTHASSGGDTDGLGGIAAQAGFNAGDGHRYFNIPGSRTADMAEVETTTNVGVPGRWTF
RIDDAQVRAGGCGHTTSVCLVLRPCLNGGKCIDDCVTGNPSYTCSCLAGFTGRRCHLDVNECA
SHPCQNGGTCTHGVNSFSCQCPAGFKGPTCESAQSPCDNKVCQNGGQCQAESSSAVCVCQAG
YTGATCETDVDECSSDPCQNGGSCVDLVGNYSCICVEPFEGPQCETGSYLVPSPCLSNPCQNGG
TCVDADEGYVCECPEGFMGLDCRERILNDCDCRNGGRCLGANTTLCQCPPGFFGLLCEFEVTA
TPCNMNTQCPDGGYCMEYGGSYLCACHTDHNISHSLPSPCDSDPCFNGGSCDAHEDSYTCECP
RGFHGRHCEKARPHLCSSGPCRNGGTCKEMGDEYRCTCPYRFTGRHCEIGKPDSCASGPCHNG
GTCFHYIGKYKCDCPPGFSGRHCEIAPSPCFRSPCMNGGTCEDLGTDFSCYCQPGYTGHRCQAE
VDCGHPEEVEHATMRFNGTHVGSVALYTCEPGFSLSALSHIRVCQPQGVWSQPPQCIEVDECRS
QPCLHGGSCQDLIAGYQCLCSPGYEGVHCELETDECQAQPCRNGGSCRDLPRAFICQCPEGFVG
IHCETEVDACASSPCQHGGRCEDGGGAYLCVCPEGFFGYNCETMSDPCFSSPCGSRGYCLASN
GSHSCTCKVGYTGKDCTKELLPPTALRVERVEESGVSISWSPPEGTTARQVLDGYAVTYASSDG
SSRRTDFVDRSRSSHQLRALAAGRAYNISVFSVKRNTNNKNDISRPAALLTRTRPRPIEDFEVTNI
SANAISVQWALHRIQHATVSRVRVSILYPEASAVQSTEVDRSVDRLTFG

Figure 4

SDHP-4

|MRPFQLDLLFLCFFLFS|QELGLQKRGCCLVLGYMAKDKFRRMNEGQVYSFSQ
QPQDQVVVSGQPVTLLCAIPEYDGFVLWIKDGLALGVGRDLSSYPQYLVVGN
HLSGEHHLKILRAELQDDAVYECQAIQAAIRSRPARLTVLVPPDDPIILGGPVISL
RAGDPLNLTCHADNAKPAASIIWLRKGEVINGATYSKTLLRDGKRESIVSTLFIS
PGDVENGQSIVCRATNKAIPGGKETSVTIDIQHPPLVNLSVEPQPVLEDNIVTFH
CSAKANPAVTQYRWAKRGHIIKEASGELYRTTVDYTYFSEPVSCEVTNALGST
NLSRTVDVYFGPRMTSEPQSLLVDLGSDAVFSCAWIGNPSLTIVWMKRGSGV
VLSNEKTLTLKSVRQEDAGKYVCRAVVPRVGAGEREVTLTVNGPPIISSTQTQ
HALHGEKGQIKCFIRSTPPPDRIAWSWKENVLESGTSGRYTVETVNTEEGVIS
TLTISNIVRADFQTIYNCTAWNSFGSDTEIIRLKEQESVPMAVIIGVAVGAGVAFL
VLMATIVAFCCARSQRNLKGVVSAKNDIRVEIVHKEPSSGREAEDHTTIKQLMM
DRGEFQQDSVLKQLEVLKEEEKEFQNLKDPTNGYYSVNTFKEHHSTPTISLSS
CQPDLRPTGKQRVPTGMSFTNIYSTLSGQGRLYDYGQRFVLGMGSSSIELCE
REFQRGSLSDSSSFLDTQCDSSVSSSGKQDGYVQFDKASKASASSSHHSQS
SSQNSDPSRPLQRRMQTHV

Figure 5

SDHF-5

|MHSRSCLPPLLLLLLVLLGSGVQG|CPSGCQCNQPQTVFCTARQGTTVPRDVPPDTVGLYIFENGI
TTLDVGCFAGLPGLQLLDLSQNQITSLPGGIFQPLVNLSNLDLTANKLHEISNETFRGLRRLERLY
LGKNRIRHIQPGAFDALDRLLELKLPDNELRVLPPLHLPRLLLLDLSHNSIPALEAGILDTANVEA
LRLAGLGLRQLDEGLFGRLLNLHDLDVYDNQLEHMPSVIQGLRGLTRLRLAGNTRIAQIRPEDL
AGLTALQELDVSNLSLQALPSDLSSLFPRLRLLAAARNPFNCLCPLSWFGPWVRENHVVLASPE
ETRCHFPPKNAGRLLLDLDYADFGCPVTTTTATVPTIRSTIREPTLSTSSQAPTWPSLTEPTTQAS
TVLSTAPPTMRPAPQPQDCPASICLNGGSCRLGARHHWECLCPEGFIGLYCESPVEQGMKPSSIP
DTPRPPPLLPLSIEPVSPTSLRVKLQRYLQGNTVQLRSLRLTYRNLSGPDKRLVTLRLPASLAEYT
VTQLRPNATYSICVTPLGAGRTPEGEEACGEANTSQAVRSNHAPVTQAREGNLPLLIAPALAAV
LLAVLAAAGAAYCVRRARATSTAQDKGQVGPGTGPLELEGVKAPLEPGSKATEGGGEALSGG
PECEVPLMGYPGPSLQGVLPAKHYI

Figure 6

SDHF-6

|MEVFLLLLTRLCLLTHLEG|HPASFKTFKQPEQVRRASPPANIHLVMTALAPLSCHYQETSSYLVP
RVVLHMPSKKSFSPQCQFPGIGPLCMTISVSELSQGSMR

Figure 8 (continuation)
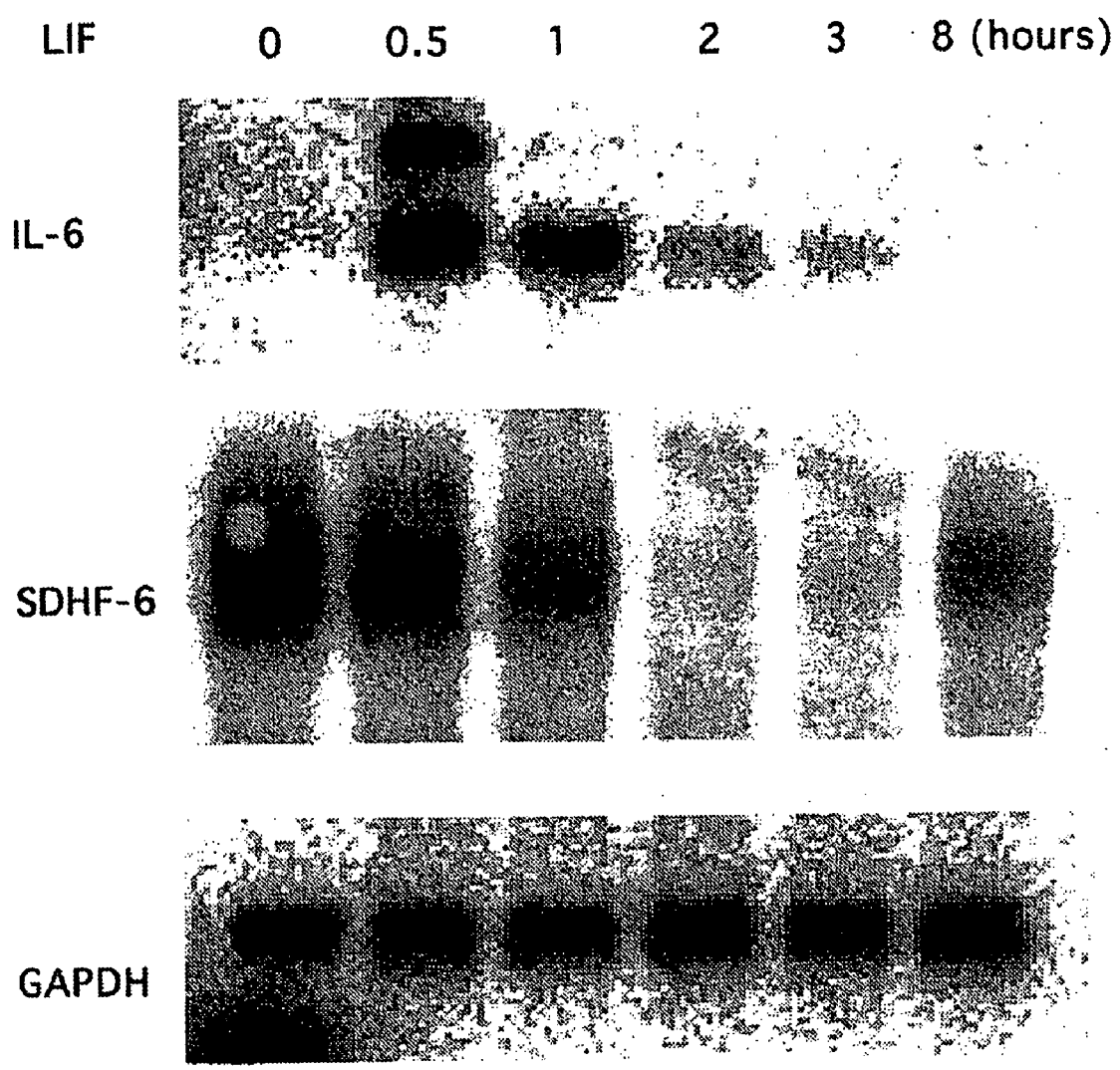

Figure 9
(a)
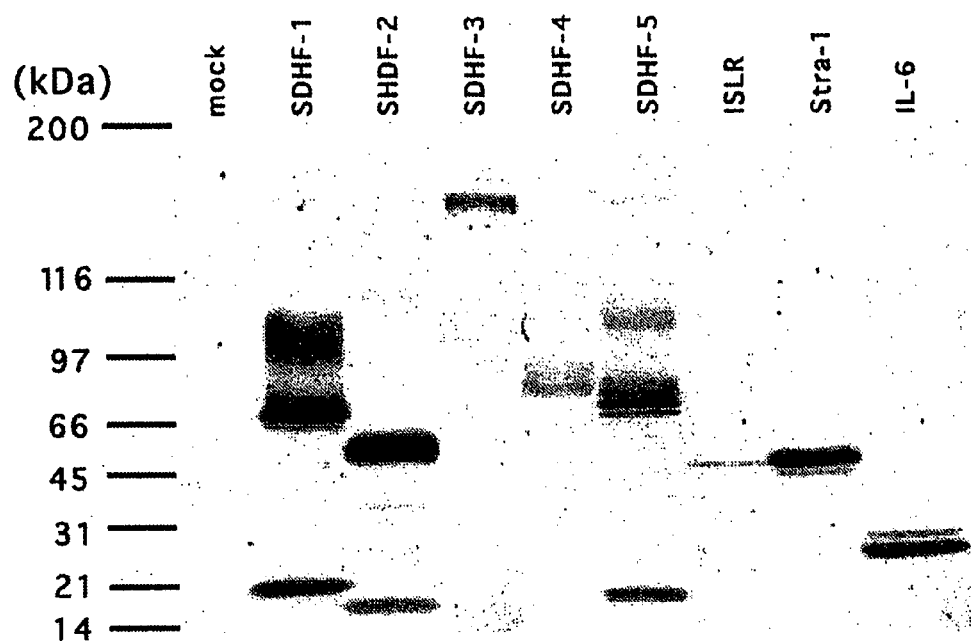
(b)
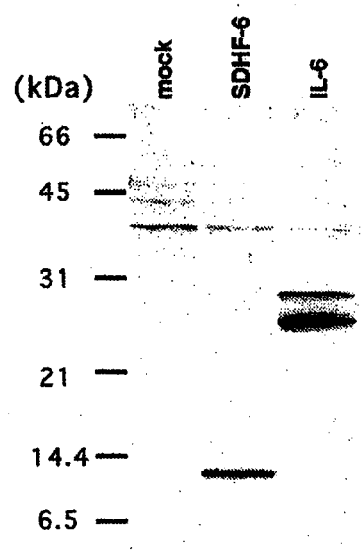

(a)

Figure 14 (continuation)
(b)
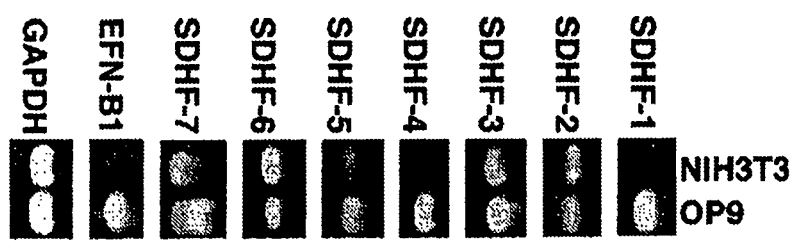
(c)
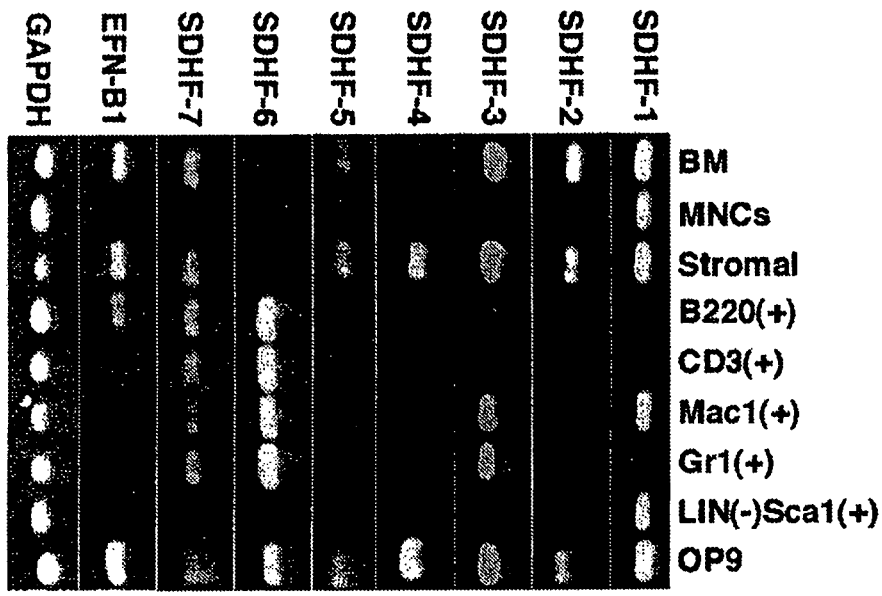

Purified Recombinant SDHF-4-△TM-hFc
(Coomassie Staining)

mock

Figure 18 (continuation)
SDHF-6
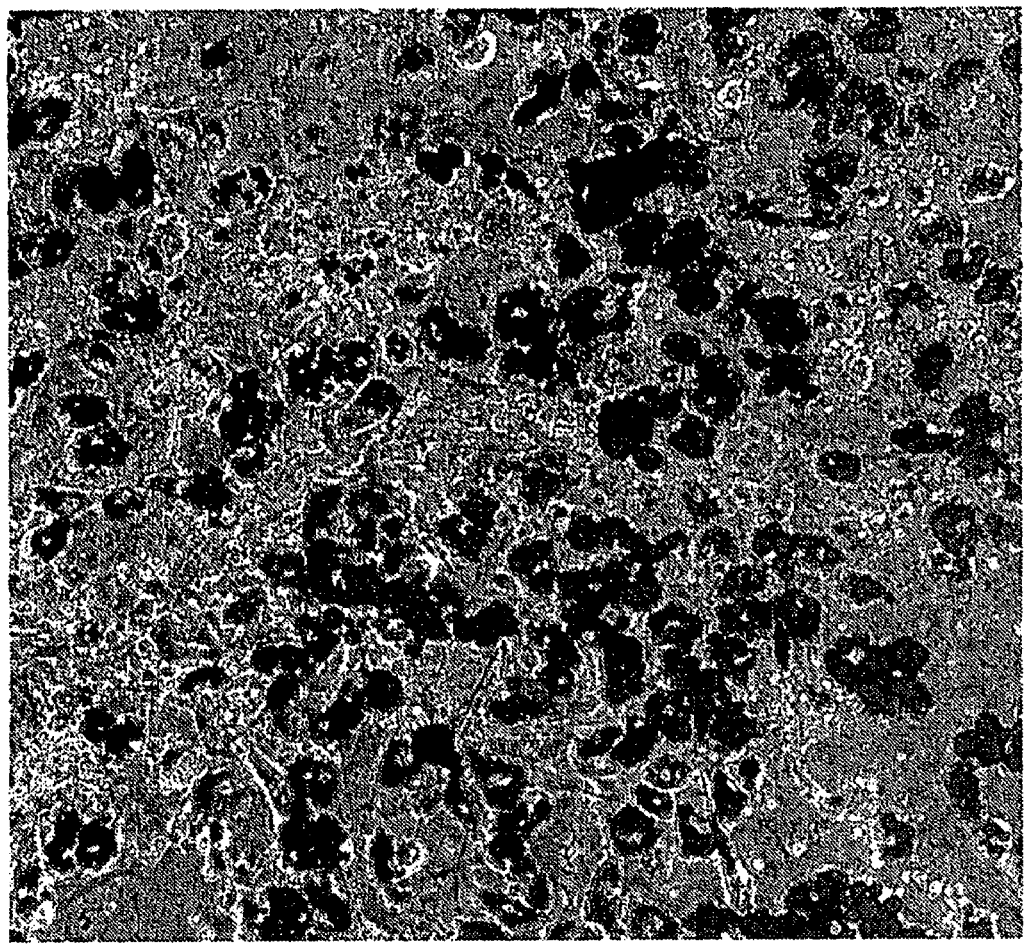

Figure 20
(a)
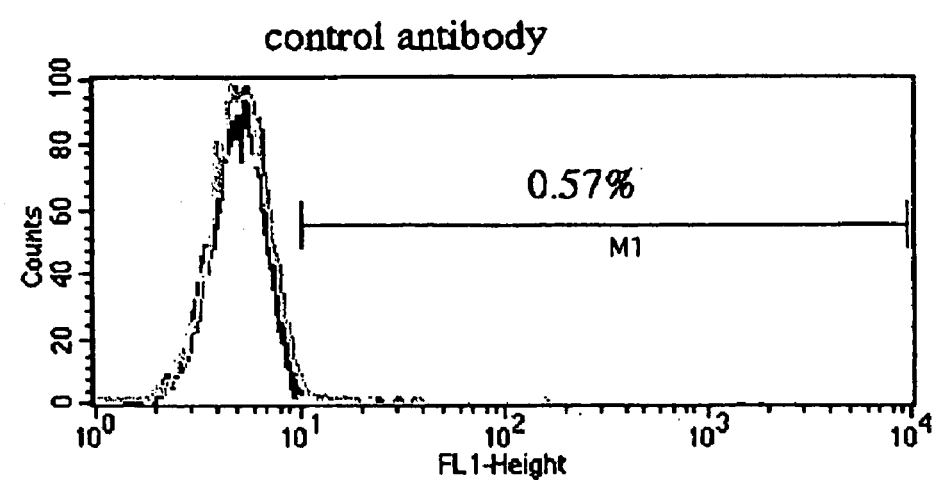
(b)
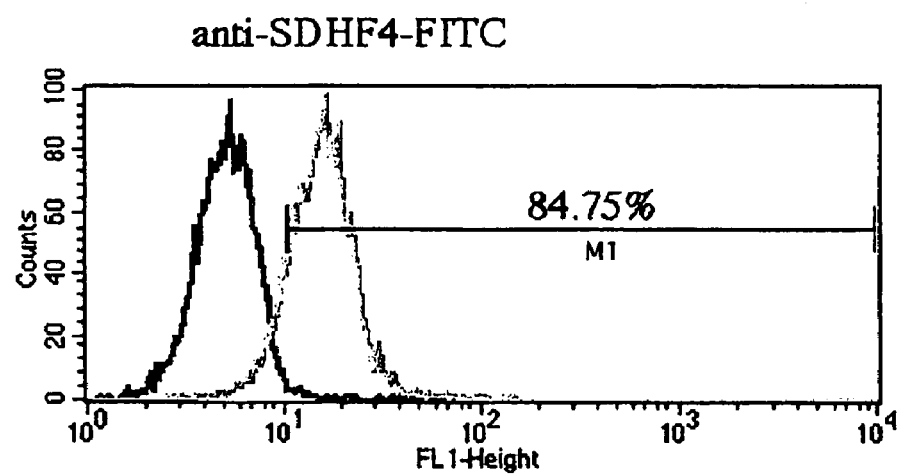

Figure 21
(a)
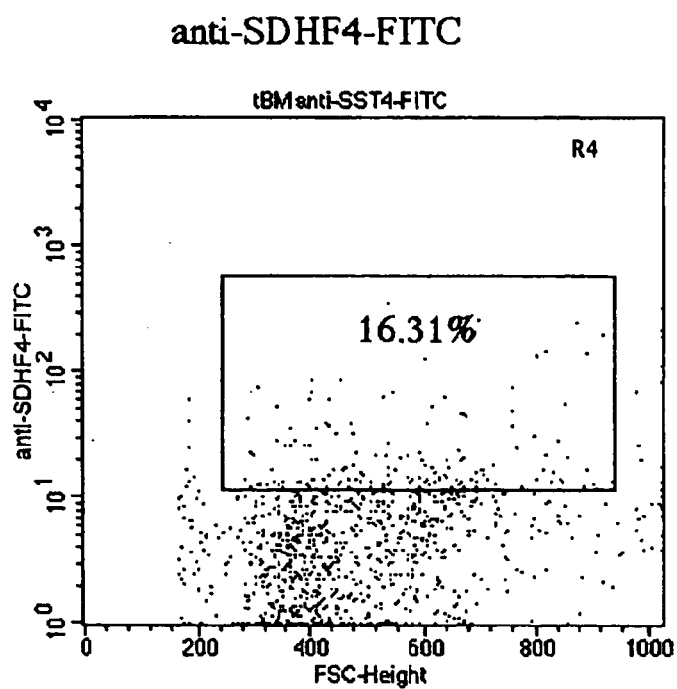
(b)
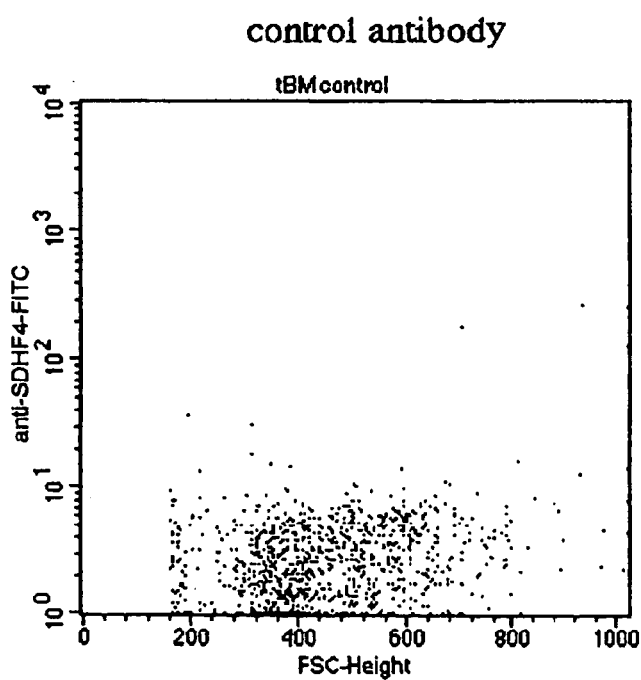

SEQUENCE LISTING

<160> NUMBER OF SEQ ID NOS: 13

<210> SEQ ID NO 1
<211> LENGTH: 3204

<212> TYPE: DNA
<213> ORGANISM: murine stromal cell

<400> SEQUENCE: 1

| | | | | | |
|---|---|---|---|---|---|
| gcggggagc | gcggcggcgc | ctccgccacc | aaactcctgg | ggctccgcgg | cgttcggagc | 60 |
| cacctcctgc | ctagcccgga | ggggctctct | taccaggctg | caacctcact | ttcccgtttt | 120 |
| tcttttcctt | taaaaaacac | ccccacctct | cttctgctca | cagcagctgg | tgcattcccg | 180 |
| gctctactct | ccggagctgc | ccatccctcc | ggctgcgggc | gaggacgcgc | gctcagcctt | 240 |
| gggcgaagca | aagaagaaaa | acttgtcaga | ggggtttctc | cagcctccac | taacctcctt | 300 |
| ctctcgggaa | caccaaccac | ccgccggggc | cagacctaag | tctgggaaag | ttcctccggt | 360 |
| gctcagcgcc | ctcttgaatc | tggaacagca | ccggcgcagc | cagtggaatt | agatctgttt | 420 |
| tgaacccagt | ggagcgcgtc | gcgggcgctc | ggaagtcacc | gtctgtgggc | gcccgggtgg | 480 |
| cgctgcctga | gaggacccgg | gagtttgccg | accctactgc | aagtgacctt | tcctcccctc | 540 |
| acttggttga | ttgtgtctca | gttggggct | gcgagggtga | caagttgcag | tgagagctcc | 600 |
| cgaagttcgg | agagggttca | gctgtctctc | cttcacttct | gttacccgga | gtgaaatcct | 660 |
| agcgaaactg | tcagaggcct | ccggatccca | cccaagactc | accagcagag | ctcggccgtg | 720 |
| tcgccccatc | cccagggata | accccggagc | cagggtctc | aagaaaaaat | tcgttgggca | 780 |
| ggggagagag | gtcgcggcag | cggcatggca | aggttccgga | gggccgacct | ggccgcagca | 840 |
| ggagttatgt | tactttgtca | cttttaaca | gaccggttcc | agttcgccca | cggggagcct | 900 |
| ggacaccata | ccaatgattg | gatttatgaa | gttacaaacg | cttttccttg | gaatgaagag | 960 |
| ggggtagaag | tggactctca | agcatacaac | cacaggtgga | aaagaaatgt | ggaccctttt | 1020 |
| aaggcagtag | acacaaacag | agccagcatg | ggccaagcct | ctccagagtc | caagggttc | 1080 |
| actgacctgc | tactggatga | cggacaggac | aataacaccc | agatagagga | ggacacggat | 1140 |
| cacaattact | acatttctcg | gatatatggt | ccagcggatt | ctgccagccg | ggatctgtgg | 1200 |
| gttaacatag | accaaatgga | aaaagacaaa | gtgaagattc | acgggatact | ttccaacact | 1260 |
| catcggcaag | ctgcaagagt | gaatctgtcc | ttcgattttc | cattttatgg | tcattttcta | 1320 |
| aatgaagtca | ctgtggcaac | tgggggtttc | atatatactg | gagaagttgt | acatcgaatg | 1380 |
| ctcacagcta | cacagtatat | agctccttta | atggcaaatt | ttgatcccag | tgtatccaga | 1440 |
| aattcaactg | tcagatattt | tgataatggc | acagctcttg | ttgtccagtg | ggaccatgtc | 1500 |
| cacctgcagg | ataattacaa | cctgggaagc | ttcacattcc | aggccacact | cctcatggac | 1560 |
| gggcgcatca | tctttggata | caaagaaatc | cctgtcttgg | tcacacagat | aagttctacc | 1620 |
| aaccatccag | tgaaagtcgg | gttgtctgat | gcatttgtcg | tggtccacag | gatccagcaa | 1680 |
| atacccaatg | ttcgaagaag | aacaatttat | gaatatcacc | gagtagaact | acaaatgtcc | 1740 |
| aaaattacca | acatctcagc | tgtggagatg | actccacttc | ccacatgtct | ccagttcaat | 1800 |
| ggttgtggcc | cttgtgtgtc | ctcgcagatt | ggtttcaact | gcagttggtg | cagcaaactt | 1860 |
| caaagatgct | ccagtggatt | tgatcgccat | cggcaggact | gggtgacag | tggatgcccg | 1920 |
| gaagaggtac | agtcaaaaga | gaagatgtgt | gagaagacag | agccaggaga | gacatctcaa | 1980 |
| actaccacga | cctcccacac | gaccaccatg | caattcaggg | tcctgaccac | caccaggaga | 2040 |
| gctgtgacat | ctcagatgcc | taccagcctg | cctacagaag | atgacacgaa | gatagcccta | 2100 |
| catctcaaag | acagtggagc | ctccacagat | gacagtgcag | ctgagaagaa | aggaggaacc | 2160 |
| ctccatgcag | gcctcattgt | tggaattctc | atcttggtcc | tcattatagc | agcggccatt | 2220 |

```
ctggtgacag tgtatatgta tcaccatcca acatcagcag ccagcatctt cttcattgag    2280
agacgcccaa gcagatggcc agcaatgaag tttcgaagag gctcaggaca ccctgcctat    2340
gcagaagttg aaccagttgg agagaaagaa ggttttattg tatcagagca gtgctaaaat    2400
tttaggacag agcagcacca gtactggctt acaggtgtta agactaaaac tttgcttatg    2460
catttaagac aaacagacac acaacccaca accacacaca aaggagccct aaactgctgt    2520
agacagaagg gcgacgagat ttggacaagc ccagcccagg aacattgaaa ggaaaactca    2580
gacttgtaca agacaccatg tacaatgatt aaagaattcc ctagtggaat gacatccatg    2640
gttcacaagg aacatctccg gtggacttgc caggagtgtg acgagatgac gatgcttttg    2700
gtttaggtgc agggttgcaa agaaatcaag gaaaaaaat atgacaataa ataaagcttt     2760
agttcacaag ggatcgacac ttttggttca aatgttcttc tctgacgtct caaagataat    2820
catgttccaa agcctgaaca ctgtcactga aaagagcaat ggtgaatgtt tcaagattgc    2880
agggaacaat agctcacaca ggagcaaaac caaacatgga tggagggttt tctatctttt    2940
ccaaacagac tatcagcaga aggattttat gttttgctct agatgtcatt gtgcagacaa    3000
gttcattact ttgtaggatg aatcttttat ttttcagaag ttcaaactct gcctgcctct    3060
tccttggtaa tgaataccat ttttgtgagc tgtgacacaa ttccctaatg ttaagctaag    3120
aaccagagag gaaggagtag ccagtgaggt ttccgttctc tcactgaaga ataaaatgcc    3180
ttctaaggtg ctgcttcctc tcct                                           3204

<210> SEQ ID NO 2
<211> LENGTH: 530
<212> TYPE: PRT
<213> ORGANISM: murine stromal cell

<400> SEQUENCE: 2

Met Ala Arg Phe Arg Arg Ala Asp Leu Ala Ala Gly Val Met Leu
 1               5                  10                  15

Leu Cys His Phe Leu Thr Asp Arg Phe Gln Phe Ala His Gly Glu Pro
                20                  25                  30

Gly His His Thr Asn Asp Trp Ile Tyr Glu Val Thr Asn Ala Phe Pro
            35                  40                  45

Trp Asn Glu Glu Gly Val Glu Val Asp Ser Gln Ala Tyr Asn His Arg
        50                  55                  60

Trp Lys Arg Asn Val Asp Pro Phe Lys Ala Val Asp Thr Asn Arg Ala
    65                  70                  75                  80

Ser Met Gly Gln Ala Ser Pro Glu Ser Lys Gly Phe Thr Asp Leu Leu
                85                  90                  95

Leu Asp Asp Gly Gln Asp Asn Asn Thr Gln Ile Glu Glu Asp Thr Asp
            100                 105                 110

His Asn Tyr Tyr Ile Ser Arg Ile Tyr Gly Pro Ala Asp Ser Ala Ser
        115                 120                 125

Arg Asp Leu Trp Val Asn Ile Asp Gln Met Glu Lys Asp Lys Val Lys
    130                 135                 140

Ile His Gly Ile Leu Ser Asn Thr His Arg Gln Ala Ala Arg Val Asn
145                 150                 155                 160

Leu Ser Phe Asp Phe Pro Phe Tyr Gly His Phe Leu Asn Glu Val Thr
                165                 170                 175

Val Ala Thr Gly Gly Phe Ile Tyr Thr Gly Glu Val Val His Arg Met
            180                 185                 190

Leu Thr Ala Thr Gln Tyr Ile Ala Pro Leu Met Ala Asn Phe Asp Pro
```

```
                195                 200                 205
Ser Val Ser Arg Asn Ser Thr Val Arg Tyr Phe Asp Asn Gly Thr Ala
    210                 215                 220

Leu Val Val Gln Trp Asp His Val His Leu Gln Asp Asn Tyr Asn Leu
225                 230                 235                 240

Gly Ser Phe Thr Phe Gln Ala Thr Leu Leu Met Asp Gly Arg Ile Ile
                245                 250                 255

Phe Gly Tyr Lys Glu Ile Pro Val Leu Val Thr Gln Ile Ser Ser Thr
            260                 265                 270

Asn His Pro Val Lys Val Gly Leu Ser Asp Ala Phe Val Val His
        275                 280                 285

Arg Ile Gln Gln Ile Pro Asn Val Arg Arg Thr Ile Tyr Glu Tyr
    290                 295                 300

His Arg Val Glu Leu Gln Met Ser Lys Ile Thr Asn Ile Ser Ala Val
305                 310                 315                 320

Glu Met Thr Pro Leu Pro Thr Cys Leu Gln Phe Asn Gly Cys Gly Pro
                325                 330                 335

Cys Val Ser Ser Gln Ile Gly Phe Asn Cys Ser Trp Cys Ser Lys Leu
            340                 345                 350

Gln Arg Cys Ser Ser Gly Phe Asp Arg His Arg Gln Asp Trp Val Asp
        355                 360                 365

Ser Gly Cys Pro Glu Glu Val Gln Ser Lys Glu Lys Met Cys Glu Lys
    370                 375                 380

Thr Glu Pro Gly Glu Thr Ser Gln Thr Thr Thr Ser His Thr Thr
385                 390                 395                 400

Thr Met Gln Phe Arg Val Leu Thr Thr Thr Arg Arg Ala Val Thr Ser
                405                 410                 415

Gln Met Pro Thr Ser Leu Pro Thr Glu Asp Asp Thr Lys Ile Ala Leu
            420                 425                 430

His Leu Lys Asp Ser Gly Ala Ser Thr Asp Asp Ser Ala Ala Glu Lys
        435                 440                 445

Lys Gly Gly Thr Leu His Ala Gly Leu Ile Val Gly Ile Leu Ile Leu
    450                 455                 460

Val Leu Ile Ile Ala Ala Ala Ile Leu Val Thr Val Tyr Met Tyr His
465                 470                 475                 480

His Pro Thr Ser Ala Ala Ser Ile Phe Phe Ile Glu Arg Arg Pro Ser
                485                 490                 495

Arg Trp Pro Ala Met Lys Phe Arg Arg Gly Ser Gly His Pro Ala Tyr
            500                 505                 510

Ala Glu Val Glu Pro Val Gly Glu Lys Glu Gly Phe Ile Val Ser Glu
        515                 520                 525

Gln Cys
    530

<210> SEQ ID NO 3
<211> LENGTH: 2137
<212> TYPE: DNA
<213> ORGANISM: murine stromal cell

<400> SEQUENCE: 3
gagagttaga gctgagtaag acaaagcacg tcccccgcag gcgccatgga gctgctgtcc    60
cgcgtcctgc tgtggaaact gctgcttctt cagagctctg cagtcctgtc ctcagggcct   120
tcagggaccg cagcagccag cagctctctg gtgtctgagt ctgtggtgag cttggcagcc   180
```

| | |
|---|---|
| ggaacccagg ctgtgctacg ctgccagagc ccccgcatgg tgtggaccca agaccggctg | 240 |
| catgatcgcc agcgcgtggt ccactgggac ctcagcgggg gccgggcag ccaacggcgc | 300 |
| cgacttgtgg atatgtattc ggcgggtgaa cagcgcgtgt acgagccgcg cgatcgcgac | 360 |
| cgcctcctgc tgtcgccttc tgctttccac gacggcaact tctcgctgct cattcgcgct | 420 |
| gtggacagag gcgatgaagg ggtgtacacc tgcaacctgc accatcacta ctgccacctc | 480 |
| gatgagagcc tggctgtgcg cctcgaggtt acagaggatc ccctattaag tcgcgcatac | 540 |
| tgggacggtg agaaggaagt gttggtggtg gcccatggcg cgccggcact gatgacctgc | 600 |
| atcaaccgtg cgcacgtgtg gactgaccgc catttagagg aggcgcagca ggtggtccat | 660 |
| tgggaccgac agctacctgg ggtgtcacac gaccgcgccg accgcctgct tgacctgtat | 720 |
| gcatctggcg agcgccgcgc ctatgggcca cccttcctgc gtgatcgcgt gtcagtgaac | 780 |
| accaacgctt ttgcacgcgg tgacttctcc ctacgcatcg atgagctgga gcgagctgat | 840 |
| gagggcatct attcctgcca cctgcaccat cactactgtg gcctccacga gcgccgagtc | 900 |
| ttccacctac aggtcacaga gcctgccttt gagccaccag ctcgtgcttc tcctggcaat | 960 |
| gggtctggtc acagcagtgc tcctagccca gatcccaccc tgacccgagg ccacagcatc | 1020 |
| atcaatgtta ttgtcccaga ggaccacaca catttcttcc agcaactggg ctatgtgttg | 1080 |
| gccacgctgc tgctcttcat cttgctgctc atcactgtag tcctggctac acgatatcgt | 1140 |
| cacagcggag gatgcaagac gtcggacaaa aaagctggga agtcaaaggg gaaggatgtg | 1200 |
| aacatggtgg agtttgctgt agccacaagg gatcaggctc catataggac tgaggacatc | 1260 |
| cagctagatt acaaaaacaa catcctgaag gagagggctg agctggccca tagtcctctg | 1320 |
| cctgccaagg atgtggatct ggataaagag ttcaggaagg agtactgcaa ataaatggac | 1380 |
| cctgagcttc tggctgggcc agcagctctg tatcaaagga catctccctg accctcctgc | 1440 |
| ggtattcctg gctcttctca gcggctggtc cgacttacct agaaacttgg cagagcagct | 1500 |
| gcctgtactt tgcccttcct agaatcgcca ccctcatct tggtgagcaa ctgtgggttc | 1560 |
| cctagagact ctggtatagt acgattgctg cccttcacct gtgcccactg atggttgtac | 1620 |
| ccccaactta aacacaacaa agatcccttg ttaatatcca ccaaatgcaa agtccctcgt | 1680 |
| ggcctcttac tgctagggtc aggaagacac ttaaaaattc cagttaagac tccctagcca | 1740 |
| ccagttaaac acattagcca ttgtcctggg gggtcttcct gagctgcatt gtgcctgtgt | 1800 |
| actgttcaga gccctgctgt tataggttct gactcatggg cccgccttgc tgctttgggc | 1860 |
| aacttgaggc tagcccaggg cccttctct gcttctgatt cctttctgcc gaatgcctcc | 1920 |
| caagagctac accagcagtt actgggtacc gtatgactct tggccttgac atccctccct | 1980 |
| aggctggagt ctggggttgg ggccccattt gtcctctgtt ttggctgaag atggggcgaa | 2040 |
| gatttggctg agtggcctat gctgtcacat caaacagcta tcatttactc ctacttggga | 2100 |
| agttttcatg tgacaataaa agatacatct gattttt | 2137 |

<210> SEQ ID NO 4
<211> LENGTH: 442
<212> TYPE: PRT
<213> ORGANISM: murine stromal cell

<400> SEQUENCE: 4

Met Glu Leu Leu Ser Arg Val Leu Leu Trp Lys Leu Leu Leu Leu Gln
1               5                   10                  15

Ser Ser Ala Val Leu Ser Ser Gly Pro Ser Gly Thr Ala Ala Ala Ser
            20                  25                  30

-continued

```
Ser Ser Leu Val Ser Glu Ser Val Ser Leu Ala Ala Gly Thr Gln
    35                  40                  45

Ala Val Leu Arg Cys Gln Ser Pro Arg Met Val Trp Thr Gln Asp Arg
    50                  55                  60

Leu His Asp Arg Gln Arg Val Val His Trp Asp Leu Ser Gly Gly Pro
65                  70                  75                  80

Gly Ser Gln Arg Arg Leu Val Asp Met Tyr Ser Ala Gly Glu Gln
                85                  90                  95

Arg Val Tyr Glu Pro Arg Asp Arg Asp Arg Leu Leu Leu Ser Pro Ser
                100                 105                 110

Ala Phe His Asp Gly Asn Phe Ser Leu Leu Ile Arg Ala Val Asp Arg
        115                 120                 125

Gly Asp Glu Gly Val Tyr Thr Cys Asn Leu His His Tyr Cys His
    130                 135                 140

Leu Asp Glu Ser Leu Ala Val Arg Leu Glu Val Thr Glu Asp Pro Leu
145                 150                 155                 160

Leu Ser Arg Ala Tyr Trp Asp Gly Glu Lys Glu Val Leu Val Val Ala
                165                 170                 175

His Gly Ala Pro Ala Leu Met Thr Cys Ile Asn Arg Ala His Val Trp
                180                 185                 190

Thr Asp Arg His Leu Glu Glu Ala Gln Gln Val Val His Trp Asp Arg
        195                 200                 205

Gln Leu Pro Gly Val Ser His Asp Arg Ala Asp Arg Leu Leu Asp Leu
    210                 215                 220

Tyr Ala Ser Gly Glu Arg Arg Ala Tyr Gly Pro Pro Phe Leu Arg Asp
225                 230                 235                 240

Arg Val Ser Val Asn Thr Asn Ala Phe Ala Arg Gly Asp Phe Ser Leu
                245                 250                 255

Arg Ile Asp Glu Leu Glu Arg Ala Asp Glu Gly Ile Tyr Ser Cys His
                260                 265                 270

Leu His His His Tyr Cys Gly Leu His Glu Arg Arg Val Phe His Leu
        275                 280                 285

Gln Val Thr Glu Pro Ala Phe Glu Pro Pro Ala Arg Ala Ser Pro Gly
    290                 295                 300

Asn Gly Ser Gly His Ser Ser Ala Pro Ser Pro Asp Pro Thr Leu Thr
305                 310                 315                 320

Arg Gly His Ser Ile Ile Asn Val Ile Val Pro Glu Asp His Thr His
                325                 330                 335

Phe Phe Gln Gln Leu Gly Tyr Val Leu Ala Thr Leu Leu Leu Phe Ile
                340                 345                 350

Leu Leu Leu Ile Thr Val Val Leu Ala Thr Arg Tyr Arg His Ser Gly
        355                 360                 365

Gly Cys Lys Thr Ser Asp Lys Lys Ala Gly Lys Ser Lys Gly Lys Asp
    370                 375                 380

Val Asn Met Val Glu Phe Ala Val Ala Thr Arg Asp Gln Ala Pro Tyr
385                 390                 395                 400

Arg Thr Glu Asp Ile Gln Leu Asp Tyr Lys Asn Asn Ile Leu Lys Glu
                405                 410                 415

Arg Ala Glu Leu Ala His Ser Pro Leu Pro Ala Lys Asp Val Asp Leu
        420                 425                 430

Asp Lys Glu Phe Arg Lys Glu Tyr Cys Lys
    435                 440
```

<210> SEQ ID NO 5
<211> LENGTH: 3766
<212> TYPE: DNA
<213> ORGANISM: murine stromal cell

<400> SEQUENCE: 5

| | | | | | |
|---|---|---|---|---|---|
| tgctattcac | gtgcctcacc | ccttcataat | ctgcgcgggt | ctccggagtg | cgacgcgagc | 60 |
| tagcggaagg | gaactgtgcg | gccagtcggt | cgtgcggtga | ctgcagccac | ctgcccgagc | 120 |
| cccgtggccc | gccctcagat | cccggcgatg | cgcctcggcg | ccgcctgggc | gctgctgctg | 180 |
| gccgcagccc | tggggctcgg | gacgcgcggg | gtgcgcgctg | ccgtggccct | cgccgacttc | 240 |
| tacccgttcg | gcacgaagcg | cggcgacacc | gtcaccccga | agcaggacga | cggcggctca | 300 |
| gggctgcaac | cactctcggt | gcccttccg | ttcttcggcg | ccgagcactc | cggactctac | 360 |
| gtgaacaata | atggaatcat | ctccttcctg | aaggaagttt | ctcagttcac | ccccgtggcc | 420 |
| ttccccatcg | ccaaagaccg | ctgtgtggta | gcagtcttct | gggcagatgt | agacaaccgg | 480 |
| cgtgcaggtg | atgtctacta | ccgggaggcc | accgacccag | ccatgctgaa | cagagccacg | 540 |
| gaggacatca | gacggtactt | tcctgagctc | ccggacttct | ctgctacctg | gttttttgtt | 600 |
| gcgacctggt | accgtgtgac | cttctttgga | ggcagcagct | cttcccccgt | taacacattc | 660 |
| caaactgtac | tcatcaccga | tggccgattc | tccttcacca | tcttcaacta | tgagtccatc | 720 |
| tgtggactac | ccggcacaca | cgccagcagc | gggggtgaca | ctgatggctt | gggaggcatt | 780 |
| gcagcccagg | caggtttcaa | cgcaggtgat | gggcaccgct | acttcaacat | ccccgggtcg | 840 |
| cgcacagcag | acatggctga | ggtggagacc | accaccaacg | tgggcgtgcc | cggccgctgg | 900 |
| acgtttagaa | tcgatgatgc | ccaggtgcgc | gcggggggct | gcggccatac | aacctctgtg | 960 |
| tgcctggtcc | tgcgtccatg | cctcaatggt | ggcaagtgca | ttgatgactg | tgtcacgggc | 1020 |
| aatccctctt | acacctgttc | ctgtctcgct | ggcttcacag | gccggagatg | ccacctggat | 1080 |
| gtgaacgagt | gtgcttccca | cccctgtcag | aatggtggga | cctgcaccca | tggtgtcaac | 1140 |
| agcttcagct | gccagtgccc | agccggcttc | aagggaccca | cctgtgaatc | ggcccaatct | 1200 |
| ccgtgtgaca | acaaagtatg | tcaaaatggt | ggccagtgcc | aggcagagag | cagctctgca | 1260 |
| gtatgtgtgt | gtcaggctgg | atacactggg | gccacctgtg | agacagatgt | ggatgaatgc | 1320 |
| agttctgacc | catgccagaa | tggggggatca | tgtgttgacc | tggttggaaa | ctacagctgt | 1380 |
| atttgtgtgg | agcccttcga | gggacctcag | tgtgagacag | gaagctacct | ggtgccttca | 1440 |
| ccctgcctct | ccaaccccctg | ccagaacggg | ggcacctgtg | tggatgctga | tgagggatac | 1500 |
| gtgtgtgaat | gccctgaagg | cttcatgggc | ttggactgca | gagagaggat | cctcaatgac | 1560 |
| tgtgactgcc | ggaacggagg | cagatgcctg | ggtgccaaca | ccaccctctg | ccagtgtcct | 1620 |
| ccaggcttct | ttgggctcct | ctgtgaattt | gaagtcacag | ccacgccctg | caacatgaac | 1680 |
| acgcagtgtc | cagatggagg | ctactgcatg | gagtatggcg | gaagctacct | atgtgcctgc | 1740 |
| cacacagacc | acaacatcag | ccactctctg | ccatcccct | gcgactcaga | cccttgcttt | 1800 |
| aatggaggtt | cctgtgacgc | ccacgaggac | tcctacacgt | gcgagtgccc | tcgtggattc | 1860 |
| cacggcaggc | actgtgagaa | agcccggcca | cacctgtgca | gctcagggcc | ctgccggaat | 1920 |
| ggaggcacat | gcaaggaaat | gggcgacgag | taccgctgca | cctgccctta | tagattcact | 1980 |
| gggagacact | gtgagattgg | aaagccagac | tcctgtgcct | ctggcccctg | tcataatggt | 2040 |
| gggacttgtt | tccactacat | tggcaaatac | aagtgtgact | gccctccagg | attctctgga | 2100 |
| cggcactgtg | agatagctcc | ctcacccctgc | ttccggagcc | catgtatgaa | tgggggtacc | 2160 |

-continued

```
tgtgaggatc tagggacaga tttctcctgc tactgccagc cagggtatac aggacaccgg    2220
tgtcaggcag aagtggactg tggtcaccct gaggaggtgg agcatgctac catgcgcttc    2280
aacggaactc acgtgggctc agtggccctg tacacatgtg agcccggctt cagcctgagt    2340
gccctcagcc atatacgtgt ctgtcagcca aagggtgtct ggagccagcc tccccagtgc    2400
attgaagtag atgagtgccg gtctcagcca tgcctgcacg gaggctcctg ccaggacctc    2460
attgctggtt accagtgcct ctgcagcccg gggtatgaag gagtccactg tgagctagag    2520
acagatgagt gccaagcaca gccatgcaga atgggggct cctgcaggga cctccccagg     2580
gctttcatct gccagtgccc tgaaggtttt gttggaatcc actgtgaaac agaggtggat    2640
gcctgtgcct ccagcccctg ccagcacgga ggccggtgtg aggacggtgg tgggcctac    2700 ctgtgcgtgt gtccagaggg cttctttgga tacaactgtg agacaatgag tgacccctgc    2760
ttctctagcc cctgtgggag ccgcggctac tgcttggcca gcaacgggtc ccacagttgt    2820
acctgcaaag tgggctacac aggcaaggac tgtaccaaag agctcctccc accaacagcc    2880 ctcaggtag aaagggtgga ggagagtggg gtctccatct cctggagtcc acccgagggc     2940
accacggcca ggcaggtgct ggatggctat gcagtcacct atgcctcctc ggatggatcg    3000
tcccggcgca cagactttgt ggaccggagc cgctcctctc accagcttcg ggccctagca    3060
gccggccgcg cctacaatat ctccgttttc tcagtcaaga gaaacacaaa caacaaaaat    3120
gacatcagca ggcctgcagc actgctcacc cgcacccgac ccgcccctat agaagacttt    3180
gaggtcacca acatttcagc caatgccatc tcagtgcagt gggctcttca caggatccag    3240
cacgccactg tcagcagggt ccgggtgtcc atcctctacc ccgaggcctc tgcggtccag    3300
tccactgagg tggacaggag tgtggaccgc ctcacatttg ggtaagagaa gatgctgcag    3360
gaatacaggt cccagagtgt tctttgtgta cctgcctgcc atccatcatc tgagggggt     3420 ggggcctgat ctgaccctca cagagttggc caggaccact atcagcaaaa taggactcct    3480
ggtcatttag agctcctaga tgctcctctc ctcctgtcca cttctgacag ggacctgctg    3540
ccagggagaa gatacactgt gcggctaacc acccttagtg ggcctggagg agctgaatat    3600
cctactgaga gcctggcttc agctccactg aacgtgtgga cccggccttt gccaccagca    3660
aacctgactg cctctcgagt cacagctacc tctgcccata tgatctggga cacccccgct    3720
ccaggtatct cactggaggc ttatgtcatc aatgtgacca caagtc                    3766
```

<210> SEQ ID NO 6
<211> LENGTH: 1065
<212> TYPE: PRT
<213> ORGANISM: murine stromal cell

<400> SEQUENCE: 6

```
Met Arg Leu Gly Ala Ala Trp Ala Leu Leu Leu Ala Ala Ala Leu Gly
1               5                   10                  15

Leu Gly Thr Arg Gly Val Arg Ala Ala Val Ala Leu Ala Asp Phe Tyr
            20                  25                  30

Pro Phe Gly Thr Lys Arg Gly Asp Thr Val Thr Pro Lys Gln Asp Asp
        35                  40                  45

Gly Gly Ser Gly Leu Gln Pro Leu Ser Val Pro Phe Pro Phe Phe Gly
    50                  55                  60

Ala Glu His Ser Gly Leu Tyr Val Asn Asn Asn Gly Ile Ile Ser Phe
65                  70                  75                  80

Leu Lys Glu Val Ser Gln Phe Thr Pro Val Ala Phe Pro Ile Ala Lys
```

-continued

```
                    85                  90                  95
Asp Arg Cys Val Val Ala Val Phe Trp Ala Asp Val Asp Asn Arg Arg
                100                 105                 110
Ala Gly Asp Val Tyr Tyr Arg Glu Ala Thr Asp Pro Ala Met Leu Asn
                115                 120                 125
Arg Ala Thr Glu Asp Ile Arg Arg Tyr Phe Pro Glu Leu Pro Asp Phe
                130                 135                 140
Ser Ala Thr Trp Val Phe Val Ala Thr Trp Tyr Arg Val Thr Phe Phe
145                 150                 155                 160
Gly Gly Ser Ser Ser Pro Val Asn Thr Phe Gln Thr Val Leu Ile
                165                 170                 175
Thr Asp Gly Arg Phe Ser Phe Thr Ile Phe Asn Tyr Glu Ser Ile Leu
                180                 185                 190
Trp Thr Thr Gly Thr His Ala Ser Ser Gly Gly Asp Thr Asp Gly Leu
                195                 200                 205
Gly Gly Ile Ala Ala Gln Ala Gly Phe Asn Ala Gly Asp Gly His Arg
                210                 215                 220
Tyr Phe Asn Ile Pro Gly Ser Arg Thr Ala Asp Met Ala Glu Val Glu
225                 230                 235                 240
Thr Thr Thr Asn Val Gly Val Pro Gly Arg Trp Thr Phe Arg Ile Asp
                245                 250                 255
Asp Ala Gln Val Arg Ala Gly Gly Cys Gly His Thr Thr Ser Val Cys
                260                 265                 270
Leu Val Leu Arg Pro Cys Leu Asn Gly Gly Lys Cys Ile Asp Asp Cys
                275                 280                 285
Val Thr Gly Asn Pro Ser Tyr Thr Cys Ser Cys Leu Ala Gly Phe Thr
                290                 295                 300
Gly Arg Arg Cys His Leu Asp Val Asn Glu Cys Ala Ser His Pro Cys
305                 310                 315                 320
Gln Asn Gly Gly Thr Cys Thr His Gly Val Asn Ser Phe Ser Cys Gln
                325                 330                 335
Cys Pro Ala Gly Phe Lys Gly Pro Thr Cys Glu Ser Ala Gln Ser Pro
                340                 345                 350
Cys Asp Asn Lys Val Cys Gln Asn Gly Gly Gln Cys Gln Ala Glu Ser
                355                 360                 365
Ser Ser Ala Val Cys Val Cys Gln Ala Gly Tyr Thr Gly Ala Thr Cys
                370                 375                 380
Glu Thr Asp Val Asp Glu Cys Ser Ser Asp Pro Cys Gln Asn Gly Gly
385                 390                 395                 400
Ser Cys Val Asp Leu Val Gly Asn Tyr Ser Cys Ile Cys Val Glu Pro
                405                 410                 415
Phe Glu Gly Pro Gln Cys Glu Thr Gly Ser Tyr Leu Val Pro Ser Pro
                420                 425                 430
Cys Leu Ser Asn Pro Cys Gln Asn Gly Gly Thr Cys Val Asp Ala Asp
                435                 440                 445
Glu Gly Tyr Val Cys Glu Cys Pro Glu Gly Phe Met Gly Leu Asp Cys
                450                 455                 460
Arg Glu Arg Ile Leu Asn Asp Cys Asp Cys Arg Asn Gly Gly Arg Cys
465                 470                 475                 480
Leu Gly Ala Asn Thr Thr Leu Cys Gln Cys Pro Pro Gly Phe Phe Gly
                485                 490                 495
Leu Leu Cys Glu Phe Glu Val Thr Ala Thr Pro Cys Asn Met Asn Thr
                500                 505                 510
```

```
Gln Cys Pro Asp Gly Gly Tyr Cys Met Glu Tyr Gly Gly Ser Tyr Leu
        515                 520                 525
Cys Ala Cys His Thr Asp His Asn Ile Ser His Ser Leu Pro Ser Pro
530                 535                 540
Cys Asp Ser Asp Pro Cys Phe Asn Gly Gly Ser Cys Asp Ala His Glu
545                 550                 555                 560
Asp Ser Tyr Thr Cys Glu Cys Pro Arg Gly Phe His Gly Arg His Cys
                565                 570                 575
Glu Lys Ala Arg Pro His Leu Cys Ser Ser Gly Pro Cys Arg Asn Gly
            580                 585                 590
Gly Thr Cys Lys Glu Met Gly Asp Glu Tyr Arg Cys Thr Cys Pro Tyr
        595                 600                 605
Arg Phe Thr Gly Arg His Cys Glu Ile Gly Lys Pro Asp Ser Cys Ala
    610                 615                 620
Ser Gly Pro Cys His Asn Gly Gly Thr Cys Phe His Tyr Ile Gly Lys
625                 630                 635                 640
Tyr Lys Cys Asp Cys Pro Pro Gly Phe Ser Gly Arg His Cys Glu Ile
                645                 650                 655
Ala Pro Ser Pro Cys Phe Arg Ser Pro Cys Met Asn Gly Gly Thr Cys
            660                 665                 670
Glu Asp Leu Gly Thr Asp Phe Ser Cys Tyr Cys Gln Pro Gly Tyr Thr
        675                 680                 685
Gly His Arg Cys Gln Ala Glu Val Asp Cys Gly His Pro Glu Glu Val
    690                 695                 700
Glu His Ala Thr Met Arg Phe Asn Gly Thr His Val Gly Ser Val Ala
705                 710                 715                 720
Leu Tyr Thr Cys Glu Pro Gly Phe Ser Leu Ser Ala Leu Ser His Ile
                725                 730                 735
Arg Val Cys Gln Pro Gln Gly Val Trp Ser Gln Pro Gln Cys Ile
            740                 745                 750
Glu Val Asp Glu Cys Arg Ser Gln Pro Cys Leu His Gly Gly Ser Cys
        755                 760                 765
Gln Asp Leu Ile Ala Gly Tyr Gln Cys Leu Cys Ser Pro Gly Tyr Glu
770                 775                 780
Gly Val His Cys Glu Leu Glu Thr Asp Glu Cys Gln Ala Gln Pro Cys
785                 790                 795                 800
Arg Asn Gly Gly Ser Cys Arg Asp Leu Pro Arg Ala Phe Ile Cys Gln
            805                 810                 815
Cys Pro Glu Gly Phe Val Gly Ile His Cys Glu Thr Glu Val Asp Ala
        820                 825                 830
Cys Ala Ser Ser Pro Cys Gln His Gly Gly Arg Cys Glu Asp Gly Gly
    835                 840                 845
Gly Ala Tyr Leu Cys Val Cys Pro Glu Gly Phe Phe Gly Tyr Asn Cys
850                 855                 860
Glu Thr Met Ser Asp Pro Cys Phe Ser Ser Pro Cys Gly Ser Arg Gly
865                 870                 875                 880
Tyr Cys Leu Ala Ser Asn Gly Ser His Ser Cys Thr Cys Lys Val Gly
                885                 890                 895
Tyr Thr Gly Lys Asp Cys Thr Lys Glu Leu Leu Pro Pro Thr Ala Leu
            900                 905                 910
Arg Val Glu Arg Val Glu Glu Ser Gly Val Ser Ile Ser Trp Ser Pro
        915                 920                 925
```

```
Pro Glu Gly Thr Thr Ala Arg Gln Val Leu Asp Gly Tyr Ala Val Thr
    930                 935                 940

Tyr Ala Ser Ser Asp Gly Ser Ser Arg Arg Thr Asp Phe Val Asp Arg
945                 950                 955                 960

Ser Arg Ser Ser His Gln Leu Arg Ala Leu Ala Ala Gly Arg Ala Tyr
                965                 970                 975

Asn Ile Ser Val Phe Ser Val Lys Arg Asn Thr Asn Lys Asn Asp
            980                 985                 990

Ile Ser Arg Pro Ala Ala Leu Leu Thr Arg Thr Arg Pro Arg Pro Ile
        995                 1000                1005

Glu Asp Phe Glu Val Thr Asn Ile Ser Ala Asn Ala Ile Ser Val Gln
    1010                1015                1020

Trp Ala Leu His Arg Ile Gln His Ala Thr Val Ser Arg Val Arg Val
1025                1030                1035                1040

Ser Ile Leu Tyr Pro Glu Ala Ser Ala Val Gln Ser Thr Glu Val Asp
                1045                1050                1055

Arg Ser Val Asp Arg Leu Thr Phe Gly
            1060                1065

<210> SEQ ID NO 7
<211> LENGTH: 3711
<212> TYPE: DNA
<213> ORGANISM: murine stromal cell

<400> SEQUENCE: 7
```

| | | |
|---|---|---|
| tgatgactgc cggatcccag tgtggtggaa ttcccgctcg ctacctcgtt cgctcgctgt | 60 |
| gggaggagcc cgccagaggt aagccgtgtg cctgggatgc aacaaccag agaatggatc | 120 |
| tgctccgagt gggcacattg ctaacgatcc cggcttcccg aggcgactga aaacaagcat | 180 |
| ttggtttcgg ctgcctgcag atacccggag acacaacgag acctaagcgg accagaggag | 240 |
| ggacagaacc gactgacaga tagatggtcg gcgcccaacc ctggaggacc ggcggcggag | 300 |
| gctgagcacc gcgagcccag ccgccgcgct ggaagagaaa ctaactgcac acccaagttg | 360 |
| cccgccggct gcccgcgcgc tgaggaatga gaccttttcca gctggatttg ctcttcctct | 420 |
| gcttcttcct cttcagtcaa gagcttggcc tccagaagag aggatgctgt ctggtactgg | 480 |
| gctacatggc caaggacaag tttcggagaa tgaatgaagg tcaagtctac tccttcagcc | 540 |
| agcaacccca ggaccaagtg gtggtgtcag acagccagt gactctgctg tgtgccatcc | 600 |
| ctgaatatga tggcttcgtc ctgtggatca aagatggctt ggctctgggt gtaggcagag | 660 |
| acctctcaag ttaccccag tacctggtgg tggggaacca cctctcagga gagcatcacc | 720 |
| tgaagatcct gagggctgag cttcaggatg atgccgtgta tgagtgccag gccatccagg | 780 |
| ctgccatccg gtcccgccct gcacgcctca ccgtcctggt gccaccagat gaccccatca | 840 |
| tcctaggggg gcctgtgatc agccttcggg caggggaccc cctcaacctc acctgccacg | 900 |
| cagacaatgc caagcctgcg gcttccatca tctggctacg taaaggagag gtcatcaatg | 960 |
| gagccaccta ctccaagacc ctgcttcgag acggcaaacg agaaagcatt gtcagcaccc | 1020 |
| tcttcatctc cccaggagac gtggaaaatg gacagagtat tgtgtgccga gccaccaaca | 1080 |
| aagccatccc cggaggaaaa gagacctctg tcaccataga catccagcat ccaccgcttg | 1140 |
| tcaacttgtc cgtggaacca cagccggtat tggaggacaa catcgtcacg ttccactgct | 1200 |
| ctgcaaaggc caaccagct gtcacccagt acaggtgggc caaacggggt cacatcatca | 1260 |
| aggaggcatc tggggagctg tataggacca cggtggacta cacatacttc tcagagcctg | 1320 |

-continued

```
tatcctgtga agtaaccaat gccctgggca gcaccaacct cagccgcaca gtggatgtat    1380
acttcggtcc tcgaatgacc tcagagcctc agtcactgct ggtagatctg ggctccgatg    1440
ctgtcttcag ctgtgcgtgg atcggcaacc cgtctctgac catcgtgtgg atgaaacgag    1500
gttctggtgt ggtcctgagc aatgaaaaga ccctaaccct caaatctgtc cgccaagagg    1560
atgctgggaa gtacgtgtgc cgggctgtgg tgccccgggt aggagctggg gagagagagg    1620
tgaccttgac tgtcaatgga ccccccatca tctccacaca cagacccag cacgccctcc     1680 acggagagaa gggccagatc aaatgcttca tccggagcac accaccgcct gaccgaattg    1740
cctggtcctg aaggagaat gtgctggagt cagggacatc agggcgctac acagtggaga     1800
cggtgaacac ggaggaggga gtcatctcca cattgaccat tagcaacatt gtgcgtgctg    1860
acttccagac catatacaac tgtacagcct ggaacagctt tggctctgac acagagatca    1920
tccgactcaa ggaacaagag tctgtaccaa tggccgtcat catcggggtg ccgtaggag     1980 ctggcgtggc cttcctcgtc ctaatggcaa ccattgtggc cttctgctgt gcccgttccc    2040
agagaaatct caaggtgtt gtatcagcca aaaatgatat tcgagtggaa attgtgcaca    2100
aggagccatc ttctggccgg gaggctgagg accacaccac cataaagcag ctgatgatgg    2160
accggggtga attccaacaa gactcggtgc tgaaacagct ggaggtcctc aaagaagagg    2220
agaaggagtt tcagaacctg aaggaccca ccaacggcta ctacagcgtc aacaccttca    2280
aagaacacca ttcaactcca accatctccc tgtccagctg ccagccagac ctgcgtccga    2340
caggcaaaca gcgtgtgccc acaggcatgt ccttcaccaa catctacagc accttgagcg    2400
gccagggccg cctctacgac tatggacaga ggtttgtgct gggcatgggc agctcttcca    2460
ttgagctttg tgagcgggag tttcagaggg gctccctcag cgacagcagc tccttcctgg    2520
acacgcagtg tgacagcagc gtcagcagca gcggcaagca agatggctac gtgcagtttg    2580
acaaggccag caaggcttct gcctcctctt cccaccattc ccagtcctct tcccagaact    2640
ccgaccccag ccgaccctg cagcggcgga tgcagactca cgtctgagga ccacgccctg     2700
tggtggggga tgggccaagg aggaggacat ggtacattct cgttctccaa ggattggggc    2760
tactttgcag aggaccctag aactggccac ctccggggtg gtctccgagc acctctgtaa    2820
acaccttcct tcaaagctct gatcaagcac aaatctggct cccaggtggg aaatggagag    2880
tatgcagctg agcggatagt gctcaaggcc tctgtctctt gctcttccct aaaggtccct    2940
caaccacctt gtcctcccat gggcactcgt ggcagctaga actttgcttt tatgaaactg    3000
ccgtccactt tcctagctcc tcttgctgcc cataagccat ccctggtgtc tgtattcctt    3060
gcagccttga ggaacggagg acttttttccc agcactgagc tgctccggag accccagcct    3120
ccccactgtg catagcctat accgcagagg ctggggcctg agaaatgcc ctgaccaaag     3180 gagcatctgc ctgggagtcc gccccactt tgtttggtgt ttgtgtctgt attcttgcag    3240
ttctgttctt ggacttgata cctctgcgct tggtggtggg actggcctat cagagtctag    3300
tgtcctcaga gctgaggaag ggaaagaggg aaaatgtgaa ctcctggaga caactggcc     3360 caacacaccc tgtgccaggc tgtgcagttc agagccctca ccgtcatcct cacccctgc     3420 cccgtgttct ccttccttc ccacagcaca atcgagctaa tccgaggagt gtgagaactc     3480
ctcttgtcag ggttttttga acagttactg aagcgtgctt cctgggagat gtgggtttga    3540
gggggtgctg aaatctaggc tggaggatga gacagactct ttcagctgat gaccacaagg    3600
aacaatgatc cattctccag tagataggac tctgtgtgca agagggacag ttttcttcac    3660
ctctttccca tcactcccca cttaagaata aacgttaggg ccattacccc c            3711
```

<210> SEQ ID NO 8
<211> LENGTH: 766
<212> TYPE: PRT
<213> ORGANISM: murine stromal cell

<400> SEQUENCE: 8

```
Met Arg Pro Phe Gln Leu Asp Leu Leu Phe Leu Cys Phe Phe Leu Phe
 1               5                  10                  15

Ser Gln Glu Leu Gly Leu Gln Lys Arg Gly Cys Cys Leu Val Leu Gly
            20                  25                  30

Tyr Met Ala Lys Asp Lys Phe Arg Arg Met Asn Glu Gly Gln Val Tyr
        35                  40                  45

Ser Phe Ser Gln Gln Pro Gln Asp Gln Val Val Ser Gly Gln Pro
    50                  55                  60

Val Thr Leu Leu Cys Ala Ile Pro Glu Tyr Asp Gly Phe Val Leu Trp
65                  70                  75                  80

Ile Lys Asp Gly Leu Ala Leu Gly Val Gly Arg Asp Leu Ser Ser Tyr
                85                  90                  95

Pro Gln Tyr Leu Val Val Gly Asn His Leu Ser Gly Glu His His Leu
            100                 105                 110

Lys Ile Leu Arg Ala Glu Leu Gln Asp Asp Ala Val Tyr Glu Cys Gln
        115                 120                 125

Ala Ile Gln Ala Ala Ile Arg Ser Arg Pro Ala Arg Leu Thr Val Leu
    130                 135                 140

Val Pro Pro Asp Asp Pro Ile Ile Leu Gly Gly Pro Val Ile Ser Leu
145                 150                 155                 160

Arg Ala Gly Asp Pro Leu Asn Leu Thr Cys His Ala Asp Asn Ala Lys
                165                 170                 175

Pro Ala Ala Ser Ile Ile Trp Leu Arg Lys Gly Glu Val Ile Asn Gly
            180                 185                 190

Ala Thr Tyr Ser Lys Thr Leu Leu Arg Asp Gly Lys Arg Glu Ser Ile
        195                 200                 205

Val Ser Thr Leu Phe Ile Ser Pro Gly Asp Val Glu Asn Gly Gln Ser
    210                 215                 220

Ile Val Cys Arg Ala Thr Asn Lys Ala Ile Pro Gly Gly Lys Glu Thr
225                 230                 235                 240

Ser Val Thr Ile Asp Ile Gln His Pro Pro Leu Val Asn Leu Ser Val
                245                 250                 255

Glu Pro Gln Pro Val Leu Glu Asp Asn Ile Val Thr Phe His Cys Ser
            260                 265                 270

Ala Lys Ala Asn Pro Ala Val Thr Gln Tyr Arg Trp Ala Lys Arg Gly
        275                 280                 285

His Ile Ile Lys Glu Ala Ser Gly Glu Leu Tyr Arg Thr Thr Val Asp
    290                 295                 300

Tyr Thr Tyr Phe Ser Glu Pro Val Ser Cys Glu Val Thr Asn Ala Leu
305                 310                 315                 320

Gly Ser Thr Asn Leu Ser Arg Thr Val Asp Val Tyr Phe Gly Pro Arg
                325                 330                 335

Met Thr Ser Glu Pro Gln Ser Leu Leu Val Asp Leu Gly Ser Asp Ala
            340                 345                 350

Val Phe Ser Cys Ala Trp Ile Gly Asn Pro Ser Leu Thr Ile Val Trp
        355                 360                 365

Met Lys Arg Gly Ser Gly Val Val Leu Ser Asn Glu Lys Thr Leu Thr
```

```
            370             375             380
Leu Lys Ser Val Arg Gln Glu Asp Ala Gly Lys Tyr Val Cys Arg Ala
385                 390                 395                 400

Val Val Pro Arg Val Gly Ala Gly Glu Arg Glu Val Thr Leu Thr Val
                405                 410                 415

Asn Gly Pro Pro Ile Ile Ser Thr Gln Thr Gln His Ala Leu His
                420                 425                 430

Gly Glu Lys Gly Gln Ile Lys Cys Phe Ile Arg Ser Thr Pro Pro
            435                 440                 445

Asp Arg Ile Ala Trp Ser Trp Lys Glu Asn Val Leu Glu Ser Gly Thr
450                 455                 460

Ser Gly Arg Tyr Thr Val Glu Thr Val Asn Thr Glu Glu Gly Val Ile
465                 470                 475                 480

Ser Thr Leu Thr Ile Ser Asn Ile Val Arg Ala Asp Phe Gln Thr Ile
                485                 490                 495

Tyr Asn Cys Thr Ala Trp Asn Ser Phe Gly Ser Asp Thr Glu Ile Ile
                500                 505                 510

Arg Leu Lys Glu Gln Glu Ser Val Pro Met Ala Val Ile Ile Gly Val
            515                 520                 525

Ala Val Gly Ala Gly Val Ala Phe Leu Val Leu Met Ala Thr Ile Val
            530                 535                 540

Ala Phe Cys Cys Ala Arg Ser Gln Arg Asn Leu Lys Gly Val Val Ser
545                 550                 555                 560

Ala Lys Asn Asp Ile Arg Val Glu Ile Val His Lys Glu Pro Ser Ser
                565                 570                 575

Gly Arg Glu Ala Glu Asp His Thr Thr Ile Lys Gln Leu Met Met Asp
            580                 585                 590

Arg Gly Glu Phe Gln Gln Asp Ser Val Leu Lys Gln Leu Glu Val Leu
            595                 600                 605

Lys Glu Glu Lys Glu Phe Gln Asn Leu Lys Asp Pro Thr Asn Gly
            610                 615                 620

Tyr Tyr Ser Val Asn Thr Phe Lys Glu His His Ser Thr Pro Thr Ile
625                 630                 635                 640

Ser Leu Ser Ser Cys Gln Pro Asp Leu Arg Pro Thr Gly Lys Gln Arg
                645                 650                 655

Val Pro Thr Gly Met Ser Phe Thr Asn Ile Tyr Ser Thr Leu Ser Gly
            660                 665                 670

Gln Gly Arg Leu Tyr Asp Tyr Gly Gln Arg Phe Val Leu Gly Met Gly
            675                 680                 685

Ser Ser Ser Ile Glu Leu Cys Glu Arg Glu Phe Gln Arg Gly Ser Leu
690                 695                 700

Ser Asp Ser Ser Ser Phe Leu Asp Thr Gln Cys Asp Ser Ser Val Ser
705                 710                 715                 720

Ser Ser Gly Lys Gln Asp Gly Tyr Val Gln Phe Asp Lys Ala Ser Lys
                725                 730                 735

Ala Ser Ala Ser Ser Ser His His Ser Gln Ser Ser Gln Asn Ser
            740                 745                 750

Asp Pro Ser Arg Pro Leu Gln Arg Met Gln Thr His Val
            755                 760                 765

<210> SEQ ID NO 9
<211> LENGTH: 2793
<212> TYPE: DNA
<213> ORGANISM: murine stromal cell
```

<400> SEQUENCE: 9

```
ggagtctgga gccggagcca gagaccgggg ctgggaaacc ccagcccggg acgggacgca      60
gcagcctctg gatcccggga ccccggacct ctcaggaccg gccagaggtg aaggactgag     120
gccccactga ggccttggac cgcaccgcct ggctccttca gccgcagtcg tctcctggga     180
cagaagatgc actccaggag ctgcctgcca cctctcctgt tgttgcttct ggtgctcctg     240
gggtctggag tacagggttg cccatcaggc tgccagtgca accagccaca gacagtcttc     300
tgcactgccc gtcagggaac acagtgccc cgagacgtgc cacctgacac agtgggcctg      360
tacatctttg agaacggcat cacgacactt gatgtgggct gttttgctgg ccttccgggc     420
ctgcagcttc tggacttgtc acagaaccag atcactagcc tgcccggggg catctttcag     480
ccacttgtta acctcagtaa cctggacctg actgccaaca aactgcacga gatctccaac     540
gagaccttcc gtggcctgcg cgcctggag cgcctctacc tgggcaagaa ccgaattcgc      600
cacatccaac cgggtgcctt cgacgcgctt gatcgcctcc tggagctcaa gctgccagac     660
aatgagcttc ggtgtgttgcc ccattgcac ttgccccgcc tgctgctgct tgacctcagc     720
cacaacagca tcccagccct ggaagccgga atactggata ccgccaatgt agaggcattg     780
aggttggctg cctagggct gcggcagctg atgaggggc ttttggccg ccttctcaac        840
ctccatgact tggatgttta tgacaaccag ttggagcata tgccatctgt gattcaaggc     900
ctgcgtggcc tgacacgcct gcggctggct ggcaacaccc gtattgccca gatacggccc     960
gaggacctcg ctggtctgac tgccctacag gaattggatg tgagcaacct aagcctgcag    1020
gccctgccca gtgacctctc gagtctcttt ccccgcctgc gcctcttagc agctgccagg    1080
aacccttca actgcttgtg ccccttgagc tggtttggtc cttgggtgcg tgagaaccat     1140
gttgtgttgg ccagccctga ggagacgcgt tgtcactttc cacccaagaa tgctggccga    1200
ctgctcctgg atctgattta tgcagatttt ggctgcccag tcaccactac cacggccaca    1260
gtacctacta aaggtctac tatcagggaa cccacacttt caacttctag ccaagctccc     1320
acctggccca gcctcacaga gccaactacc caggcctcca ccgtactatc gactgcccca    1380
ccaaccatga ggccagctcc tcagccccag gactgtccag catccatctg cctgaatggt    1440
ggtagctgcc gtttgggagc aagacaccac tgggagtgcc tatgccctga ggcttcatt     1500
ggcctgtact gtgagagtcc agtggagcaa gggatgaagc ccagctccat accagacact    1560
ccaaggcccc ctccactgct gcctctcagc attgagccgg tgagccccac ctccttgcgt    1620
gtgaagctgc agcgctactt gcagggtaac actgtgcagc tacggagcct ccggctcacc    1680
tatcgcaacc tgtctggccc tgacaaacga ctggtgacat acggctgcc tgcttcactt     1740
gcagagtata cagtcaccca gctgcgaccc aatgccacct attctatctg tgtcacaccc    1800
ttgggagctg acggacacc tgaaggtgag gaggcctgtg ggaggccaa cacttcccag      1860
gcagtccgct ctaaccatgc cccagttacc caggcccgtg agggcaacct gccactcctc    1920
attgcgcctg ccctggctgc tgtacttctg gctgtgttag ccgctgcagg ggcagcctac    1980
tgtgtgcggc gggcacgggc aacttctaca gctcaggaca aagggcaggt ggggccaggg    2040
actggacccc tggaactaga gggggtgaaa gcccctttgg agccaggctc caaggcaaca    2100
gagggaggtg gggaggcttt gtcaggtggt cctgaatgtg aggtgcctct tatgggctac    2160
ccagggccca gccttcaggg ggtcctccct gctaagcact acatttagac tggtgagaaa    2220
gagcagccag ggggtcaggc tttcagtcac caccctcctg ctgccacaga aggaagttct    2280
```

-continued

```
cagtatacac cacagtgcac gtgcatgatg gagctgtggg accctctctg ggctgggtct    2340
catctgtaag ctgctacagc ccagatgaac tctgccagcc gccagtgcat ccagtacagc    2400
gcctgccatc ttgtgcaatg tgcaaccctg ggatgtgagc cctgccatgt gctggtaaca    2460
tggctaggca tgttgggctt cccaaaccat ggagtctggt aaccagtgaa ggaagccccc    2520
agaaataatg agtggggaag gtactagggc actggccttg gcctcaaaag tgcaggcaca    2580
cttgaaactg gaaggaagg tgctctgggc acatgtggat ttgcttctat tgttttgttt    2640
tgttttttct aatgtattta taaaagatct tttcccattt atgctgggaa agtgtttttc    2700
aaactcagtg acaaggactt tggttttgt aagactgttg atgatatgaa ggccttttgt    2760
aagaaaataa aaaataaagt aaattgcctg tct                                 2793
```

<210> SEQ ID NO 10
<211> LENGTH: 673
<212> TYPE: PRT
<213> ORGANISM: murine stromal cell

<400> SEQUENCE: 10

```
Met His Ser Arg Ser Cys Leu Pro Pro Leu Leu Leu Leu Leu Val
 1               5                  10                  15

Leu Leu Gly Ser Gly Val Gln Gly Cys Pro Ser Gly Cys Gln Cys Asn
                20                  25                  30

Gln Pro Gln Thr Val Phe Cys Thr Ala Arg Gln Gly Thr Thr Val Pro
            35                  40                  45

Arg Asp Val Pro Pro Asp Thr Val Gly Leu Tyr Ile Phe Glu Asn Gly
        50                  55                  60

Ile Thr Thr Leu Asp Val Gly Cys Phe Ala Gly Leu Pro Gly Leu Gln
 65                  70                  75                  80

Leu Leu Asp Leu Ser Gln Asn Gln Ile Thr Ser Leu Pro Gly Gly Ile
                85                  90                  95

Phe Gln Pro Leu Val Asn Leu Ser Asn Leu Asp Leu Thr Ala Asn Lys
            100                 105                 110

Leu His Glu Ile Ser Asn Glu Thr Phe Arg Gly Leu Arg Arg Leu Glu
        115                 120                 125

Arg Leu Tyr Leu Gly Lys Asn Arg Ile Arg His Ile Gln Pro Gly Ala
    130                 135                 140

Phe Asp Ala Leu Asp Arg Leu Leu Glu Leu Lys Leu Pro Asp Asn Glu
145                 150                 155                 160

Leu Arg Val Leu Pro Pro Leu His Leu Pro Arg Leu Leu Leu Leu Asp
                165                 170                 175

Leu Ser His Asn Ser Ile Pro Ala Leu Glu Ala Gly Ile Leu Asp Thr
            180                 185                 190

Ala Asn Val Glu Ala Leu Arg Leu Ala Gly Leu Gly Leu Arg Gln Leu
        195                 200                 205

Asp Glu Gly Leu Phe Gly Arg Leu Leu Asn Leu His Asp Leu Asp Val
    210                 215                 220

Tyr Asp Asn Gln Leu Glu His Met Pro Ser Val Ile Gln Gly Leu Arg
225                 230                 235                 240

Gly Leu Thr Arg Leu Arg Leu Ala Gly Asn Thr Arg Ile Ala Gln Ile
                245                 250                 255

Arg Pro Glu Asp Leu Ala Gly Leu Thr Ala Leu Gln Glu Leu Asp Val
            260                 265                 270

Ser Asn Leu Ser Leu Gln Ala Leu Pro Ser Asp Leu Ser Ser Leu Phe
        275                 280                 285
```

```
Pro Arg Leu Arg Leu Leu Ala Ala Arg Asn Pro Phe Asn Cys Leu
    290                 295                 300

Cys Pro Leu Ser Trp Phe Gly Pro Trp Val Arg Glu Asn His Val Val
305                 310                 315                 320

Leu Ala Ser Pro Glu Glu Thr Arg Cys His Phe Pro Lys Asn Ala
            325                 330                 335

Gly Arg Leu Leu Leu Asp Leu Asp Tyr Ala Asp Phe Gly Cys Pro Val
                340                 345                 350

Thr Thr Thr Thr Ala Thr Val Pro Thr Ile Arg Ser Thr Ile Arg Glu
            355                 360                 365

Pro Thr Leu Ser Thr Ser Ser Gln Ala Pro Thr Trp Pro Ser Leu Thr
    370                 375                 380

Glu Pro Thr Thr Gln Ala Ser Thr Val Leu Ser Thr Ala Pro Pro Thr
385                 390                 395                 400

Met Arg Pro Ala Pro Gln Pro Gln Asp Cys Pro Ala Ser Ile Cys Leu
                405                 410                 415

Asn Gly Gly Ser Cys Arg Leu Gly Ala Arg His His Trp Glu Cys Leu
            420                 425                 430

Cys Pro Glu Gly Phe Ile Gly Leu Tyr Cys Glu Ser Pro Val Glu Gln
            435                 440                 445

Gly Met Lys Pro Ser Ser Ile Pro Asp Thr Pro Arg Pro Pro Pro Leu
    450                 455                 460

Leu Pro Leu Ser Ile Glu Pro Val Ser Pro Thr Ser Leu Arg Val Lys
465                 470                 475                 480

Leu Gln Arg Tyr Leu Gln Gly Asn Thr Val Gln Leu Arg Ser Leu Arg
                485                 490                 495

Leu Thr Tyr Arg Asn Leu Ser Gly Pro Asp Lys Arg Leu Val Thr Leu
            500                 505                 510

Arg Leu Pro Ala Ser Leu Ala Glu Tyr Thr Val Thr Gln Leu Arg Pro
    515                 520                 525

Asn Ala Thr Tyr Ser Ile Cys Val Thr Pro Leu Gly Ala Gly Arg Thr
530                 535                 540

Pro Glu Gly Glu Glu Ala Cys Gly Glu Ala Asn Thr Ser Gln Ala Val
545                 550                 555                 560

Arg Ser Asn His Ala Pro Val Thr Gln Ala Arg Glu Gly Asn Leu Pro
                565                 570                 575

Leu Leu Ile Ala Pro Ala Leu Ala Ala Val Leu Leu Ala Val Leu Ala
            580                 585                 590

Ala Ala Gly Ala Ala Tyr Cys Val Arg Arg Ala Arg Ala Thr Ser Thr
    595                 600                 605

Ala Gln Asp Lys Gly Gln Val Gly Pro Gly Thr Gly Pro Leu Glu Leu
    610                 615                 620

Glu Gly Val Lys Ala Pro Leu Glu Pro Gly Ser Lys Ala Thr Glu Gly
625                 630                 635                 640

Gly Gly Glu Ala Leu Ser Gly Gly Pro Glu Cys Glu Val Pro Leu Met
                645                 650                 655

Gly Tyr Pro Gly Pro Ser Leu Gln Gly Val Leu Pro Ala Lys His Tyr
            660                 665                 670

Ile

<210> SEQ ID NO 11
<211> LENGTH: 1312
<212> TYPE: DNA
```

<213> ORGANISM: murine stromal cell

<400> SEQUENCE: 11

```
cataccgtgt gcggtttcct gttcttcttc ccttctgttt ttttttcttc gtttatttca      60
ctgttcgaat ctttgggttc tatctcttga tgtgtaggat tcctttccgt gtgtaccaat     120
tgttatgtct ttctgttatg gcatacctca gtcgtccttc cagccgtcta tttggtgttc     180
tagctgccaa atagtgaagt gatagaatac ccaaccccac tagctgtgcc atactctttc     240
caggcatgag gaagagactg aaccatcatc atctcaggct tgactcaggg atgaccagag     300
gcccagtgtt taatgcttgg ttctactaac tatatggaag gctgtcttta ctctccatag     360
ctaagaaccc cagcccagca tggaagtctt tttgttacta ctgacaaggt tgtgcctgct     420
cacacacctg gaaggacacc ctgcttcttt caagactttc aagcagccag agcaggtgag     480
gagagcatca cctcctgcta acatccacct tgtcatgaca gcactagccc cctgtcctg     540
tcactaccaa gaaactagtt cttacttggt tccccgagtt gtcctccata tgccttccaa     600
aaaatccttt tctccccaat gtcagtttcc tggtatagga cctctttgta tgactatctc     660
agttagcgag ctcagccaag gcagcatgag gtaaatatgg gatcattatc accctagcc     720
acagcacttc acaactgtac tatctgtcat ggctcttact gtcaccatgt ggtaagccat     780
cttcccctat ctttaagtca cccatttttaa aggtatccaa atacatggta tattgctttc     840
aggatgttcc actgtatcaa atagggtttc cacactataa aatattgttt cctatagtac     900
agtaagattt tttcttaaca ctttgtctca catataaatg agagctaaaa acaaatgcc     960
aaggaaagac aggataaagc tctctacttc tggcttgatg attcttgagt agatctacgt    1020
ttgtagttgg taagttagtc aagagtgtcc ctgacctttg aaagttagca agaaatagcc    1080
acacatgtag catcagtact gatttgtcat tattgatcca gacggttgat cattaatgga    1140
gtcccttcat ttccagctgg ttctagggct atgctttcgc ccaaaagaaa gctatcatca    1200
tagccaaggg agcataccctg ttcttttcac aaagaagaat ttaaaaaccc tgtcttaaca    1260
agtctttaaa aagaatgct gtgaaaggtt ggtctcataa agaaaaaag cc              1312
```

<210> SEQ ID NO 12
<211> LENGTH: 104
<212> TYPE: PRT
<213> ORGANISM: murine stromal cell

<400> SEQUENCE: 12

```
Met Glu Val Phe Leu Leu Leu Thr Arg Leu Cys Leu Leu Thr His
  1               5                  10                  15

Leu Glu Gly His Pro Ala Ser Phe Lys Thr Phe Lys Gln Pro Glu Gln
                 20                  25                  30

Val Arg Arg Ala Ser Pro Pro Ala Asn Ile His Leu Val Met Thr Ala
             35                  40                  45

Leu Ala Pro Leu Ser Cys His Tyr Gln Glu Thr Ser Ser Tyr Leu Val
         50                  55                  60

Pro Arg Val Val Leu His Met Pro Ser Lys Lys Ser Phe Ser Pro Gln
     65                  70                  75                  80

Cys Gln Phe Pro Gly Ile Gly Pro Leu Cys Met Thr Ile Ser Val Ser
                         85                  90                  95

Glu Leu Ser Gln Gly Ser Met Arg
                100
```

<210> SEQ ID NO 13

<211> LENGTH: 428
<212> TYPE: PRT
<213> ORGANISM: murine stromal cell
<220> FEATURE:
<221> NAME/KEY: SIGNAL
<222> LOCATION: (1)..(18)

<400> SEQUENCE: 13

```
Met Arg Ala Leu Cys Leu Leu Cys Trp Ala Val Leu Leu Asn Leu Val
 1               5                  10                  15

Arg Ala Cys Pro Glu Pro Cys Asp Cys Gly Glu Lys Tyr Gly Phe Gln
            20                  25                  30

Ile Ala Asp Cys Ala Tyr Arg Asp Leu Glu Gly Val Pro Pro Gly Phe
        35                  40                  45

Pro Ala Asn Val Thr Thr Leu Ser Leu Ser Ala Asn Arg Leu Pro Gly
    50                  55                  60

Leu Pro Glu Gly Ala Phe Arg Glu Val Pro Leu Leu Gln Ser Leu Trp
65                  70                  75                  80

Leu Ala His Asn Glu Ile Arg Ser Val Ala Ile Gly Ala Leu Ala Pro
                85                  90                  95

Leu Ser His Leu Lys Ser Leu Asp Leu Ser His Asn Leu Leu Ser Glu
           100                 105                 110

Phe Ala Trp Ser Asp Leu His Asn Leu Ser Ala Leu Gln Leu Leu Lys
       115                 120                 125

Met Asp Ser Asn Glu Leu Ala Phe Ile Pro Arg Asp Ala Phe Ser Ser
130                 135                 140

Leu Ser Ala Leu Arg Ser Leu Gln Leu Asn His Asn Arg Leu His Ala
145                 150                 155                 160

Leu Ala Glu Gly Thr Phe Ala Pro Leu Thr Ala Leu Ser His Leu Gln
                165                 170                 175

Ile Asn Asp Asn Pro Phe Asp Cys Thr Cys Gly Ile Val Trp Phe Lys
           180                 185                 190

Thr Trp Ala Leu Ala Ser Ala Val Ser Ile Pro Glu Gln Asp Asn Ile
       195                 200                 205

Ala Cys Thr Thr Pro His Val Leu Lys Gly Ile Pro Leu Gly Arg Leu
210                 215                 220

Pro Pro Leu Pro Cys Ser Ala Pro Ser Val Gln Leu Ser Tyr Gln Pro
225                 230                 235                 240

Ser Gln Asp Gly Ala Glu Leu Arg Pro Gly Phe Val Leu Ala Leu His
                245                 250                 255

Cys Asp Val Asp Gly Gln Pro Val Pro Gln Leu His Trp His Ile His
           260                 265                 270

Thr Pro Gly Gly Thr Val Glu Ile Ala Ser Pro Asn Val Gly Thr Asp
       275                 280                 285

Gly Arg Ala Leu Pro Gly Ala Leu Ala Thr Ser Gly Gln Pro Arg Phe
290                 295                 300

Gln Ala Phe Ala Asn Gly Ser Leu Leu Ile Pro Asp Phe Gly Lys Leu
305                 310                 315                 320

Glu Glu Gly Thr Tyr Ser Cys Leu Ala Thr Asn Glu Leu Gly Ser Ala
                325                 330                 335

Glu Ser Ser Val Asn Val Ala Leu Ala Thr Pro Gly Glu Gly Gly Glu
           340                 345                 350

Asp Ala Val Gly His Lys Phe His Gly Lys Ala Val Glu Gly Lys Gly
       355                 360                 365

Cys Tyr Thr Val Asp Asn Glu Val Gln Pro Ser Gly Pro Glu Asp Asn
```

-continued

```
                    370                 375                 380
Val Val Ile Ile Tyr Leu Ser Arg Ala Gly Pro Pro Glu Ala Ala Ile
385                 390                 395                 400

Ala Ala Asp Gly Arg Pro Ala Gln Gln Phe Ser Gly Ile Leu Leu Leu
                405                 410                 415

Gly Gln Ser Leu Leu Val Leu Ser Phe Phe Tyr Phe
                420                 425
```

HEMATOPOIETIC STEM CELL PROLIFERATION REGULATORS AND POLYNUCLEOTIDES ENCODING THE SAME

FIELD OF THE INVENTION

The present invention relates to a novel hematopoietic stem cell proliferation regulators produced by a bone marrow stromal cell which is considered to form a hematopoietic microenvironment (niche) and regulate the proliferation and the differentiation of hematopoietic stem cells or hematopoietic precursor cells via hematopoietic factors and adhesion molecules, as well as a gene (polynucleotide) encoding the same.

BACKGROUND OF THE INVENTION

Hematopoietic stem cells present in a bone marrow, and mesencymal stem cells serve to maintain an adult body life by being differentiated over their entire life span into respective blood cells, bones, cartilages, fat cells and the like the supply of which is done by them continuously. Recently, these tissue-specific stem cells were reported to be capable of being differentiated also into the cells of multiple organs (nerve, liver, lung, intestinal tracts, cardiac muscles, muscles and the like) under a certain condition, and it is considered to be very important to understand their proliferation mechanisms also in view of the application to a transplantation therapy and a regenerative medicine.

A large number of attempts have been made heretofore to accomplish an in vitro amplification of a hematopoietic stem cell, and some of them were successful to some extent. In bone marrow stromal cells as considered to form a hematopoietic microenvironment (niche) and regulate proliferation and differentiation of hematopoietic precursor cells via hematopoietic factors and an adhesion molecules. Those reported as the hematopoietic factors produced by the stromal cell are cytokines such as IL-3 and IL-6, SCF, receptor-type tyrosine kinase ligands such as an Flt-3 ligand (Gibson, F. M. et al., Br J Haematol 1995), a differentiation-inhibiting factor Notch ligand jagged-1 (Varnum-Finney, B. et al., Blood 1998).

However, most of the membrane-binding factors and adhesion molecules required for the hematopoiesis described above are considered to be unidentified. While it is impossible to culture a hematopoietic stem cell for a prolonged period only by combining currently known factors with each other, such a culture is possible for a certain time period in the presence of stromal cells which are hematopoiesis-supporting cells, suggesting that the stromal cells may express hematopoiesis-related proteins which have not been identified.

SUMMARY OF THE INVENTION

Accordingly, an objective of the invention is to solve the above-mentioned problems by analyzing hematopoietic cell proliferation-regulating factors produced by stromal cells, constructing a cDNA library and isolating novel hematopoiesis-related genes whereby enabling a future application to an in vitro amplification of the hematopoietic stem cells, a transplantation therapy against hematopoietic malignancies regenerative therapy care using stem cells and a gene therapy.

We made an effort to accomplish the above-mentioned objective and finally discovered, in a bone marrow stromal cells, novel genes encoding proteins having a hematopoietic stem cell proliferation-regulating activity, whereby establishing the invention.

Thus, the invention relates to a gene encoding a protein (a) or (b):

(a) an amino acid sequence represented by one SEQ ID No. selected from the group consisting of SEQ ID Nos. 2, 4, 6, 8, 10 and 12, (b) a protein having a hematopoietic stem cell proliferation-regulating activity which consists of an amino acid sequence formed as a result of a deletion, substitution or addition of one or several amino acids in the amino acid sequence (a).

The invention also relates to a gene comprising a DNA (a) or (b):

(a) a DNA consisting of the base sequence represented by one SEQ ID No. selected from the group consisting of SEQ ID Nos. 1, 3, 5, 7, 9 and 11, (b) a DNA encoding a protein having a hematopoietic stem cell proliferation-regulating activity which hybridizes under a stringent condition with a DNA consisting of the base sequence (a).

As used herein, the term "hematopoietic stem cell proliferation-regulating activity" includes an ability of amplifying or increasing the proliferation of a hematopoietic stem cell and an ability of rather inhibiting the proliferation of the hematopoietic stem cell, and means any function for exerting some effect on the proliferation of the hematopoietic stem cell. The term "hematopoietic stem cell" means not only a hematopoietic stem cell in its narrow sense but also myelocytic, erythroblastic, megakaryocytic and lymphocytic precursor cells which have been differentiated once and can be detected for example in the Cobblestone area forming cell (CAFC) described below.

The invention also relates to a protein encoded by such a gene or DNA. Since the 6 proteins which have been identified for the first time by the invention are derived from a stromal cell and each have a hematopoietic stem cell proliferation-regulating activity as shown in Examples described below, they are designated as SDHF (Stromal cell Derived Hematopoietic Factor)-1, SDHF-2, SDHF-3, SDHF-4, SDHF-5 and SDHF-6. The base sequences encoding these proteins and the corresponding amino acid sequences are represented by SEQ ID Nos. 1 and 2, SEQ ID Nos. 3 and 4, SEQ ID Nos. 5 and 6, SEQ ID Nos. 7 and 8, SEQ ID Nos. 9 and 10 and SEQ ID Nos. 11 and 12.

The invention further relates to a recombinant expression vehicle comprising at least any one of the genes described above, a transformant obtained by the transformation with said expression vehicle, and a method for producing any of the proteins described above comprising the culture of said transformant.

The invention further relates to a method for regulating the hematopoietic stem cell-proliferating activity of a stromal cell comprising the transformation of said stromal cell with at least any one of the genes described above. In said transformed stromal cell, a gene of the invention is expressed and its hematopoietic stem cell proliferation-regulating activity results in an amplification or increase or reduction in the hematopoietic stem cell-proliferating activity of said stromal cell. The transformation can be conducted for example by a method known to those skilled in the art using a recombinant expression vehicle described above.

The base sequence encoding the amino acid sequence represented by SEQ ID No. 13 has already been reported (1999, Genomics 61 (1), pp37-43), and referred to as an ISLR whose function has never been known heretofore, but it has proven by us for the first time here to have a hematopoietic stem cell proliferation-regulating activity as shown in the EXAMPLES described below.

Accordingly, the invention relates to a method for modifying the hematopoietic stem cell proliferation-regulating activity of a stromal cell consisting of a transformation of said stromal cell with a gene encoding a protein (a) or (b)
(a) an amino acid sequence represented by SEQ ID No. 13,
(b) a protein having a hematopoietic stem cell proliferation-regulating activity which consists of an amino acid sequence formed as a result of a deletion, substitution or addition of one or several amino acids in the amino acid sequence (a). The transformation can be conducted for example by a method known to those skilled in the art using a recombinant expression vehicle described above.

The invention further relates to a composition for regulating a hematopoietic stem cell proliferation comprising as an active ingredient at least one protein selected from SDHF-1 to SDHF-6 and ISLR described above.

As used herein the term "hematopoietic stem cell-proliferating activity" means a function for exerting some effect on the proliferation of a hematopoietic stem cell, and the term "regulation" means any change in said activity such as an amplification or increase, or rather inhibition and the like.

The invention further relates to various antibodies such as polyclonal antibodies and monoclonal antibodies directed to respective proteins according to the invention such as SDHF-1, -2, -3, -4, -5 and -6 described above.

FIG. 23 shows schematic views of the molecular structures of SDHF-1 to SDHF-6 according to the invention.

BRIEF DESCRIPTION OF THE DRAWINGS

FIG. 1 shows the amino acid sequence of SDHF-1 (SEQ ID NO: 2).

FIG. 2 shows the amino acid sequence of SDHF-2 (SEQ ID NO: 4).

FIG. 3 shows the amino acid sequence of SDHF-3 (SEQ ID NO: 6).

FIG. 4 shows the amino acid sequence of SDHF-4 (SEQ ID NO: 8).

FIG. 5 shows the amino acid sequence of SDHF-5 (SEQ ID NO: 10).

FIG. 6 shows the amino acid sequence of SDHF-6 (SEQ ID NO: 12).

FIGS. 9a and 9b show the results obtained by a western analysis.

FIGS. 20a and 20b show the results of a FACS calibur (Becton Dickinson) analysis of a CHO-k1 cell allowed to express SDHF-4 after labelling the purified antibody described above with FITC.

FIGS. 21a and 21b show the results of a sorting of a cell expressing SDHF-4 using a FACS Vantage (Becton Dickinson) after staining a myelocyte of a C57BL/6J mouse using the same antibody.

BEST MODE FOR CARRYING OUT THE INVENTION

Figure 7:
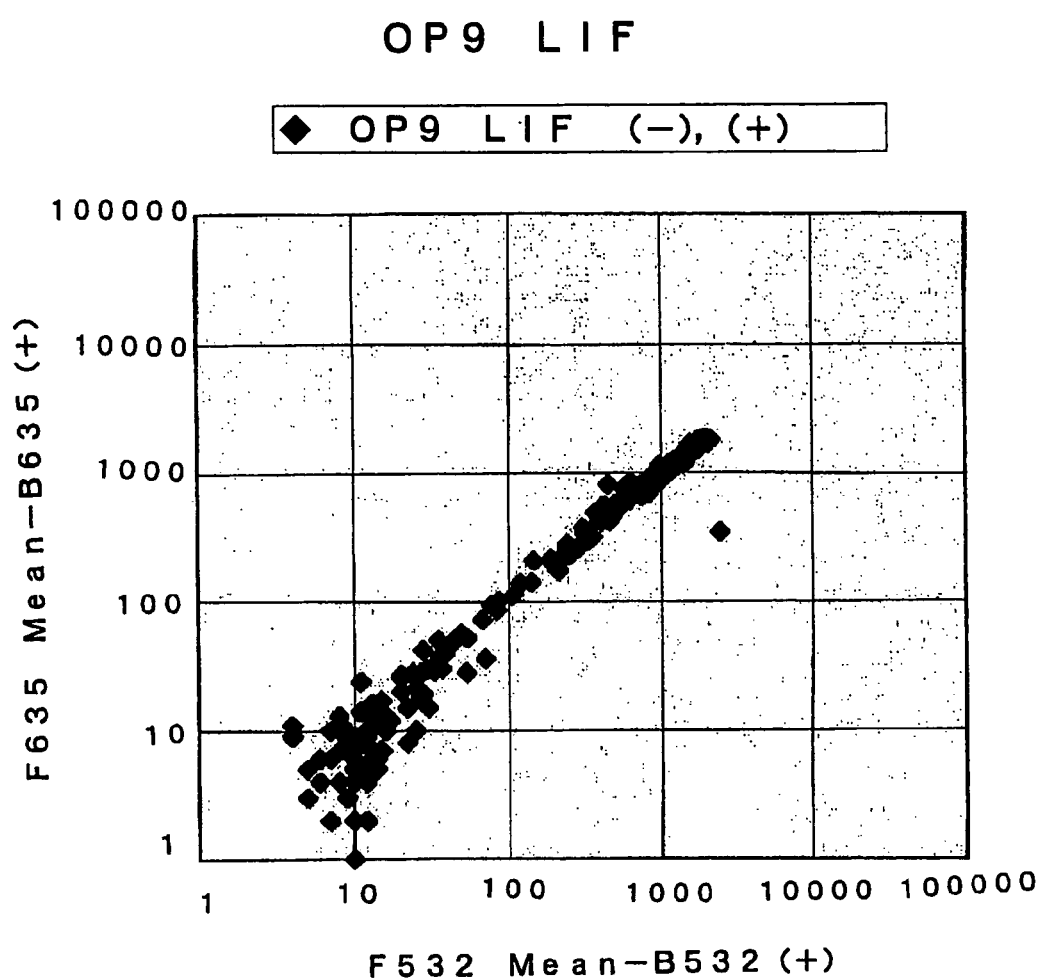
FIG. 7 shows the results obtained by a micro array method.

A gene or DNA of the invention can be prepared for example by a method shown in the EXAMPLES described below based on a cDNA library prepared from an mRNA derived from a stromal cell such as a mouse stromal cell line OP9 which has been stimulated by a leukemia-inhibiting factor (LIF) during culture.

Alternatively, it can be prepared also by a chemical synthesis using a procedure known in the art based on the sequence information disclosed in this specification. Those skilled in the art may accomplish the deletion, substitution or addition of one or several amino acids in a certain amino acid sequence by means of a method known per se in the art.

In the invention, a specific gene or DNA can be hybridized under a stringent condition with regard to various parameters such as salt concentrations at a suitable temperature in a buffer solution known to those skilled in the art.

An example of the DNA which hybridizes under such a stringent condition with a gene or DNA of the invention and which encodes a protein having a hematopoietic stem cell proliferation-regulating activity is a DNA whose homology with such a gene is 70% or more, preferably 90% or more.

A DNA obtained by binding a gene or DNA of the invention appropriately to any of various sequences known to those skilled in the art in a gene recombination procedure such as regulatory factors including promoters and enhancers, restricted enzyme sites, selection marker (marker enzyme) gene and the like is also encompassed by the invention.

An expression vehicle such as a recombinant plasmid vector having a gene, DNA or a DNA molecule of the invention described above or a recombinant virus vector employing a retrovirus and the like, and a transformant of a microorganism such as *Escherichia coli* and an eukaryotic cell such as a mouse COS-7 cell or a mouse stromal cell OP9, which contains such an expression vehicle and has thus been transformed, are also encompassed by the invention. These DNA molecules, expression vehicles and transformants can readily be prepared by a method known in the art. In addition, a protein of the invention can be readily produced by those skilled in the art by culturing an above-mentioned transformant by a known method and purifying the culture product.

A hematopoietic stem cell proliferation regulation activating composition of the invention comprising a protein described above as an active ingredient may also contain, as appropriate, other cytokines known as hematopoietic factors, as well as suitable carriers and auxiliary agents known in the art. The amounts and the ratios of the protein of the invention as an active ingredient and other components may be selected by those skilled in the art depending on the purpose of use.

The antibodies such as polyclonal and monoclonal antibodies of the invention directed to the respective proteins of the invention such as SDHF-1, -2, -3, -4, -5 and -6 can be produced by any known method. For example, a polyclonal antibody can readily be produced by inoculating each protein described above or its partial peptide as an immunogen to any experimental animal such as a rabbit. A monoclonal antibody can readily be obtained by subjecting an antibody-producing cell prepared similarly using such an immunogen to a cell fusion with a suitable parent cell (immortalized cell line) by a method known in the art to yield a hybridoma followed by screening the hybridoma for a clone which reacts specifically with each protein. The partial peptide corresponds to any partial amino acid sequence in the respective protein, and the number of the amino acids is not limited particularly but preferably is at least 10, and usually is within the range from 10 to 20. In view of the reactivity with each protein, it is preferable to select a partial peptide employed as an immunogen from the extracellular region of the respective protein.

Such an antibody can be used in a procedure for isolating or purifying various adult cells such as bone marrow stem cells, mesencymal stem cells and nervous stem cell as well as stem cell-supporting cells (stromal cells) such as a bone marrow hematopoiesis-supporting cells. Such an isolation or purification may be conducted by various means known to those skilled in the art, such as an affinity column purification or a FACS sorting.

EXAMPLES

The invention is further described referring to the following EXAMPLES, which are not intended to restrict the technical scope of the invention.

cDNA Library Construction and Signal Sequence Trap (SST) Method

A mouse stromal cell line OP9 is incubated in Alpha-MEM medium supplemented with 20% fetal bovine serum. APLAT-E cell (2000, Morita et al., Gene Therapy vol. 7, 1063-6) was incubated in DMEM supplemented with 10% fetal bovine serum. The extraction of polyA RNA from the OP9 cell was conducted using an Invitrogen FAST TRACK 2.0 mRNA Isolation Kit in accordance with the protocol attached thereto. As a starting material for a cDNA library, 5 µg of polyA RNA extracted from $1 \times 10^8$ OP9 cells stimulated for 60 minutes at 37° C. with 10 ng/ml of mouse leukemia inhibitory factor (LIF) was employed. The cDNA library was constructed using a SUPERSCRIPT II (Invitrogen) using random hexamers as primers. The resultant cDNA library was combined with a BstXI adapter primer (Invitrogen) and integrated into the BstXI site of a retrovirus vector pMX-SST vector (1999, Kojima et al., Nat Biotech vol. 17, p. 487) to construct a plasmid library.

The cDNA library obtained was introduced into a PLAT-E cell using FuGene 6 (Roche), and then recovered in the form of a retrovirus in the supernatant. The resultant retrovirus cDNA library was infected to a Ba/F3 cell which is an interleukin 3 (IL-3)-dependent mouse pro-B cell. The pMX-SST vector has a signal peptide-deficient constantly activated c-Mp1 gene, and the cmp1 gene is activated when a library-derived gene has a signal peptide and consequently the Ba/F3 cell is immortalized in the absence of IL-3 (1999, Kojima et al., Nat Biotech vol. 17, p. 487-90). The retrovirus library-infected Ba/F3 cell was deprived of IL-3, and incubated in a 96-well plate at the density of 1000 cell/well, and then the proliferated cells were isolated and the genome DNA was extracted. Since a signal peptide-carrying gene has been inserted into the genome DNA of the Ba/F3 cell via the retrovirus, it was recovered by a genome DNA PCR (LA-Taq, TAKARA, 98° C. for 20 sec. 68° C. for 300 sec.: 35 cycles) using the primers (GGGGGTGGACCATC-CTCTA, CGCGCAGCTGTAAACGGTAG) designed based on the sequence of the pMX-SST vector.

Gene Sequencing

Since a signal peptide-carrying clone was obtained as a DNA fragment by the PCR described above, its DNA sequence was determined using an ABI 373A sequencer. The resultant PCR fragment was purified by a PCR purification kit (Quiagen) to be deplete the primers, and the sequences were determined by a dye termination method in accordance with the protocol by ABI. The resultant sequence information was analyzed by an NCBI BLAST program (http://www.ncbi.nlm.nih.gov/BLAST/) whereby judging whether the sequences were known or unknown. A part of an unknown sequence was determined by a 3' RACE method using primers designed based on the sequences obtained. The 3' RACE method is a strategy for identifying an unknown gene to the extent of the polyA region by a PCR method using the primers designed on the basis of the above-mentioned PCR clone sequences as well as oligo dT primers. The DNA sequence of any resultant PCR fragment was determined as described above using an ABI 373A sequencer.

As a result, the genes of 234 clones in total including known and unknown ones were isolated by the SST method described above. They included 181 known genes, 42 unknown genes and 11 genes which could not be analyzed. The known genes included 49 proliferation factors, 23 receptors, 71 adhesion molecules and 38 others.

Among the unknown genes, 6 SDHF (stromal cell derived hematopoietic factor) genes of the invention and ISLR were included. As shown in FIGS. 1 to 6 and in SEQ ID No. 13, the N terminal of the amino acid sequence encoded by 6 SDHF and ISLR genes contained a signal peptide (region surrounded by a rectangular frame). The results obtained as described above are summarized in Table 1 and Table 2.

TABLE 1

| | |
|---|---|
| SDF-1-alpha | 27 |
| ISLR (immunoglobulin superfamily containing leucine-rich repeat) | 11 |
| ADAMTS-1 (secretory protein, metalloprotease) | 10 |
| SDHF-1 | 7 |
| collagen a1(V) | 7 |
| Fractalkine | 7 |
| amyloid beta protein precursor | 6 |
| collagen alpha1 (VI) | 6 |
| gp130 | 6 |
| thrombospondin 1 | 6 |
| CCK4 (RTK), homologue | 5 |
| collagen, alpha-2 collagen VI | 5 |
| collagen, pro-alpha1 (II) collagen chain | 5 |
| fibronectin | 5 |
| SPARC-related protein (SRG) | 5 |
| syndecan | 5 |
| amyloid precursor-like protein 2 | 4 |
| BiP, immunoglobulin heavy chain binding protein | 4 |
| insulin-like growth factor binding protein 4 | 4 |
| interleukin 1 receptor accessory protein. | 4 |
| protein disulfide isomerase (ERp59) | 4 |
| Cyr61, CTGF, IGFBP10 | 3 |
| lysyl oxidase (Lox) | 3 |
| SDHF-2 | 2 |
| collagen, alpha-2 type IV collagen | 2 |
| collagen, pro-alpha-2(I) collagen | 2 |
| collagenase, type IV collagenase | 2 |
| osteopontin | 2 |
| P2B/LAMP-1 | 2 |
| PDGFR beta | 2 |
| vimentin | 2 |
| SDHF-3 | 1 |
| SDHF-4 | 1 |
| SDHF-5 | 1 |
| SDHF-6 | 1 |
| SDHF-7 | 1 |
| SDHF-8 | 1 |

TABLE 2

| Unknown clones | |
|---|---|
| ISLR | 11 |
| SDHF-1 | 7 |
| SDHF-2 | 2 |
| SDHF-3 | 1 |
| SDHF-4 | 1 |
| SDHF-5 | 1 |
| SDHF-6 | 1 |
| SDHF-7 | 1 |
| SDHF-8 | 1 |
| others | 16 |
| | 42 |
| Known clones | |
| FACTORS | |
| SDF-1-alpha | 27 |
| Fractalkine | 7 |
| insulin-like growth factor binding protein 4 | 4 |
| Cyr61, CTGF, IGFBP 10 | 3 |
| lysyl oxidase (Lox) | 3 |
| osteopontin | 2 |
| alpha inhibin | 1 |
| S1-5, T16 homologue, | 1 |
| STRA-1/EFLN B2 | 1 |
| | 49 |
| RECEPTORS | |
| gp130 | 6 |
| CCK4 (RTK), homologue | 5 |
| IL-1 receptor accessory protein. | 4 |
| PDGFR beta | 2 |

TABLE 2-continued

| | |
|---|---|
| Fc receptor | 2 |
| clone: 2-63 | 1 |
| FGF receptor | 1 |
| LDL receptor | 1 |
| ROBO-1 | 1 |
| | 23 |
| Adhesion & Matrix proteins | |
| ADAMTS-1 (secretory protein, metalloprotease) | 10 |
| collagen a1(V) | 7 |
| amyloid beta protein precursor | 6 |
| collagen alpha1 (VI) | 6 |
| thrombospondin 1 | 6 |
| collagen, alpha-2 collagen VI | 5 |
| collagen, pro-alpha1 (II) collagen chain | 5 |
| fibronectin | 5 |
| SPARC-related protein (SRG) | 5 |
| collagen, alpha-2 type IV collagen | 2 |
| collagen, pro-alpha-2(I) collagen | 2 |
| collagenase, type IV collagenase | 2 |
| cadherin-11 (OSF-4) | 1 |
| calpain small subunit | 1 |
| calumenin | 1 |
| collagen, type 1 procollagen C-proteinase enhancer protein | 1 |
| entactin/nidogen | 1 |
| extracellular matrix associated protein (Sc1) | 1 |
| metalloproteinase 1 | 1 |
| nucleobindin | 1 |
| thrombomodulin | 1 |
| type 1 procollagen C-proteinase enhancer protein | 1 |
| | 71 |
| Others | |
| | 31 |
| not membranous | 7 |
| TOTAL | 223 |

Microarray Method

All PCR fragments obtained by the signal sequence trap method were spotted onto glass slides (procedure heretofore being conducted by HOKKAIDO SYSTEM SCIENCE), and the change in the expression was investigated using a fluorescence-labeled cDNA probe prepared from the cells adjusted under the condition before and after the stimulation of the OP9 cells with 10 ng/ml LIF at 37° C. for 60 minutes. The probe was subjected to a reverse transcription using a SuperScript II employing oligo dT primers from the polyA RNA extracted as described above, and then purified using a Microcon 30 (Millipore) labeled by means of the integration of a Fluorolink Cy-dUTP. The results obtained are shown in FIG. 7.

Northern Blotting

Figure 8:
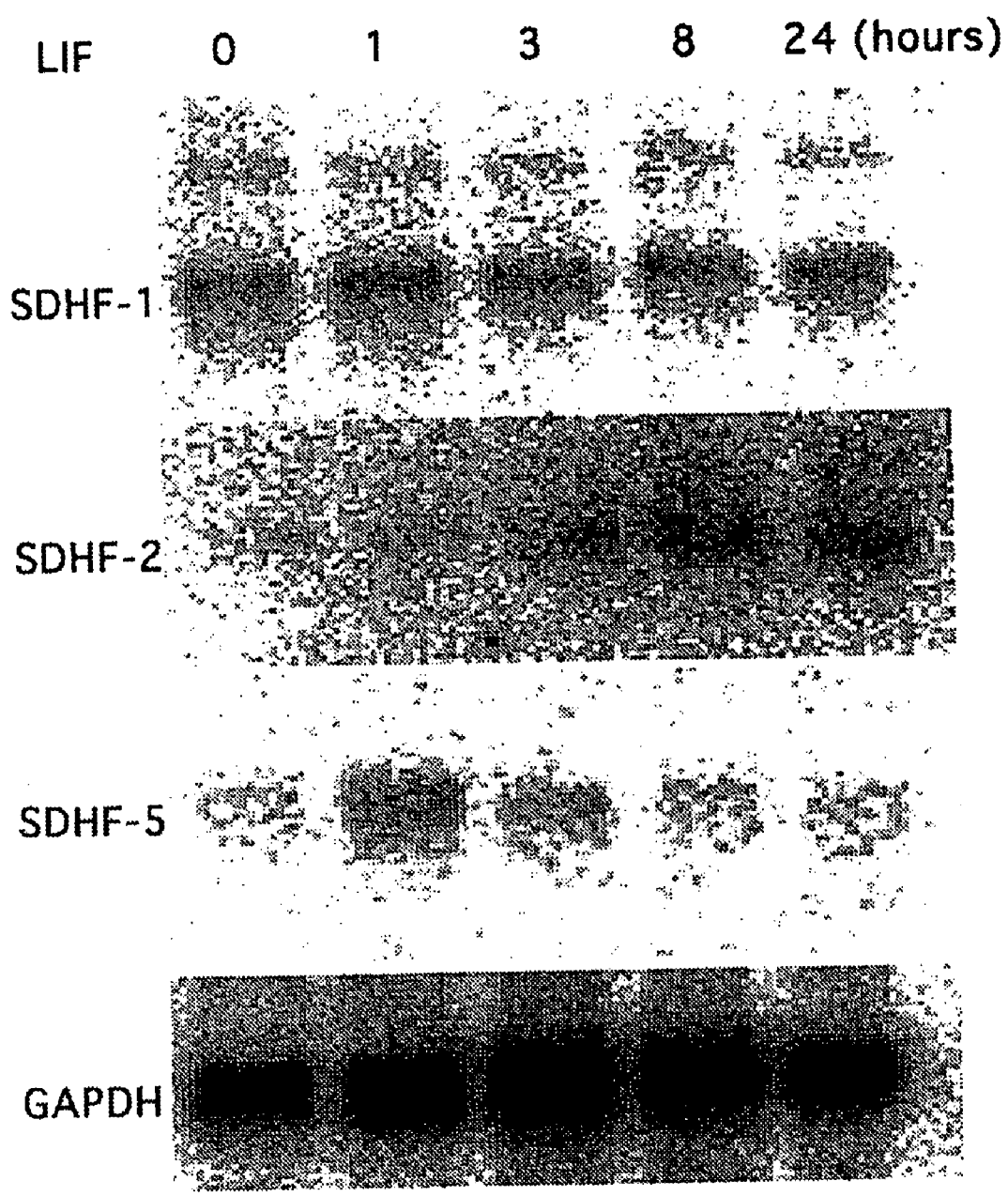
FIG. 8 shows the results obtained by a northern blotting.

The OP9 cells were stimulated with 10 ng/ml of LIF at 37° C. for 60 minutes, and then after 0 minutes, 30 minutes, 1 hour, 3 hours, 8 hours and 24 hours, the total RNA was extracted using a Trizol reagent (Invitrogen) in accordance with the protocol. The total RNA thus extracted was examined for the concentration, and then a 10 µg aliquot was subjected to an electrophoresis on a 1% agarose gel, transferred onto a Hybond N (Amersham), and subjected to a northern blotting by a standard method using the respective gene DNA fragment as a probe. As a result, an increase in the expression of each of SDHF-1, SDHF-2 and SDHF-5 genes was observed as evident from FIG. 8. On the contrary, SDHF-6 gene exhibited a reduction in the expression.

Western Blotting

From the sequence of the entire length of a gene thus obtained, an amino acid-encoding region (open reading frame: ORF) was determined, and its carboxyl terminal was tagged with a FLAG tag sequence (DYKDDDDK) by a PCR method. All of these cDNAs were subcloned into an expression vector pUC-CAGGS which was then expressed transiently in COS-7 cells using FuGene 6 (Roche). The western blotting was conducted as reported previously (1995, Ueno, JBC Vol. 270, pp. 20135-42). The cells were solubilized with a Triton lysis buffer (0.5% (v/v), Triton X-100, 50 mM Tris-HCl, pH 7.4, 2 mM PMSF, 10 U/ml aprotinin, 1 mM EDTA) and then a 50 μg lysate was subjected to an SDS-polyacrylamide gel electrophoresis (PAGE), transferred to an Immobilon-P membrane, and then detected using an anti-FLAG antibody, M2 (Sigma). As a result, any of the genes of the invention was expressed in the COS7 cells and exhibited the bands in the western blotting.

Immunostaining

Figure 10:
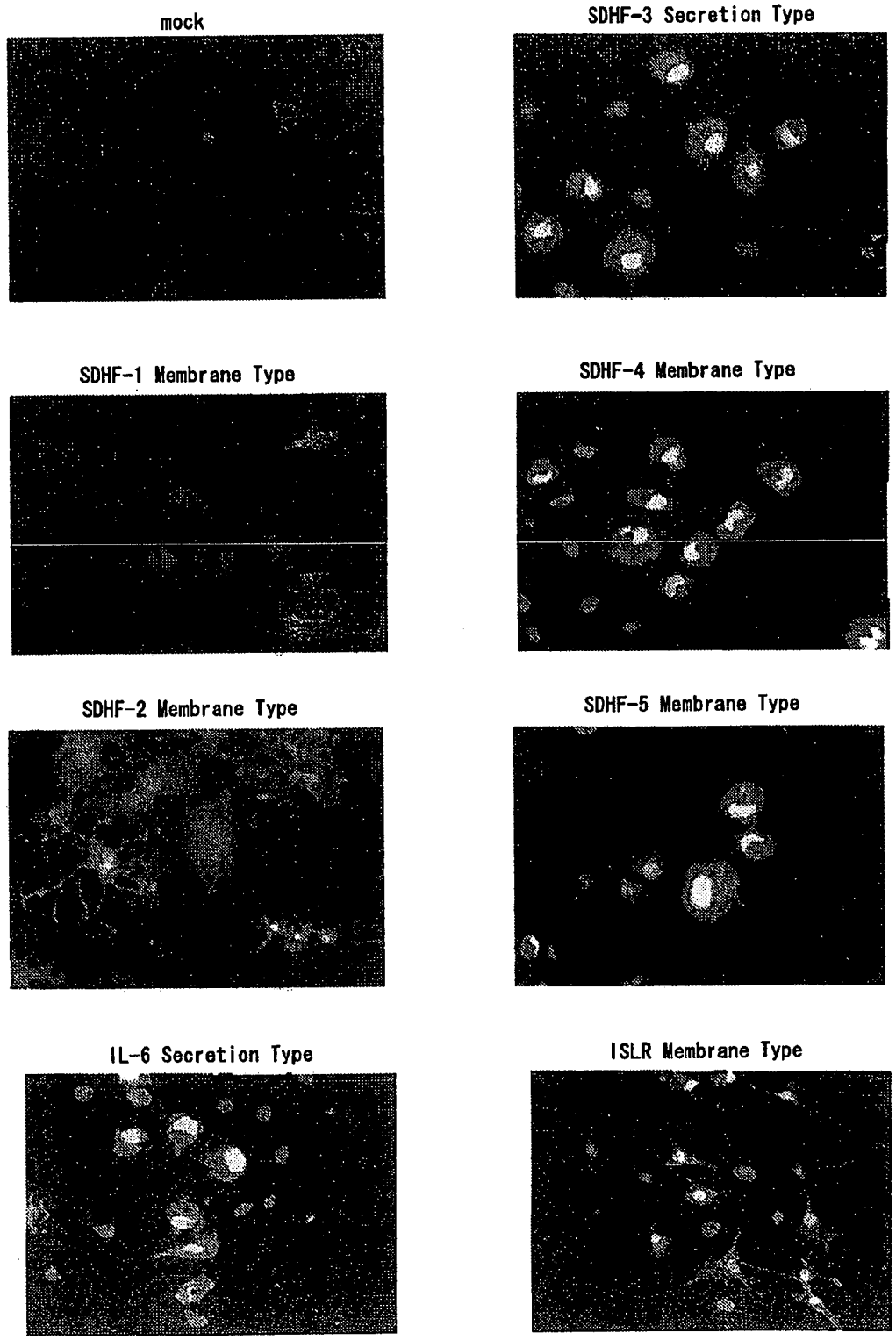
FIG. 10 shows the results obtained by an immunostaining method.

Genes tagged with a FLAG peptide were expressed transiently in the COS-7 cells using a FuGene reagent (see above), fixed in a 3.7% formaldehyde, subjected to a permeabilization with a 1% NP40, and stained with an anti-FLAG antibody (secondary antibody: Texas Red-labeled anti-mouse antibody, Jackson). The nucleus was stained with DAPI (FUNAKOSHI). The results are shown in FIG. 10.

Cobblestone Area Forming Cell Assay: CAFC Assay

A gene obtained as described above in the OP9 cells was transduced into a retrovirus vector (pMX-puro), which were inoculated to a 6-well dish at the density of $2.5 \times 10^5$, and incubated overnight and then inoculated with $1 \times 10^5$ of the bone marrow cells obtained from the femoral bones of 5 to 8-week old C57BL/6mice, and the number of the CAFCs formed was counted after 6 days.

Results of CAFC Analysis

Figure 11:
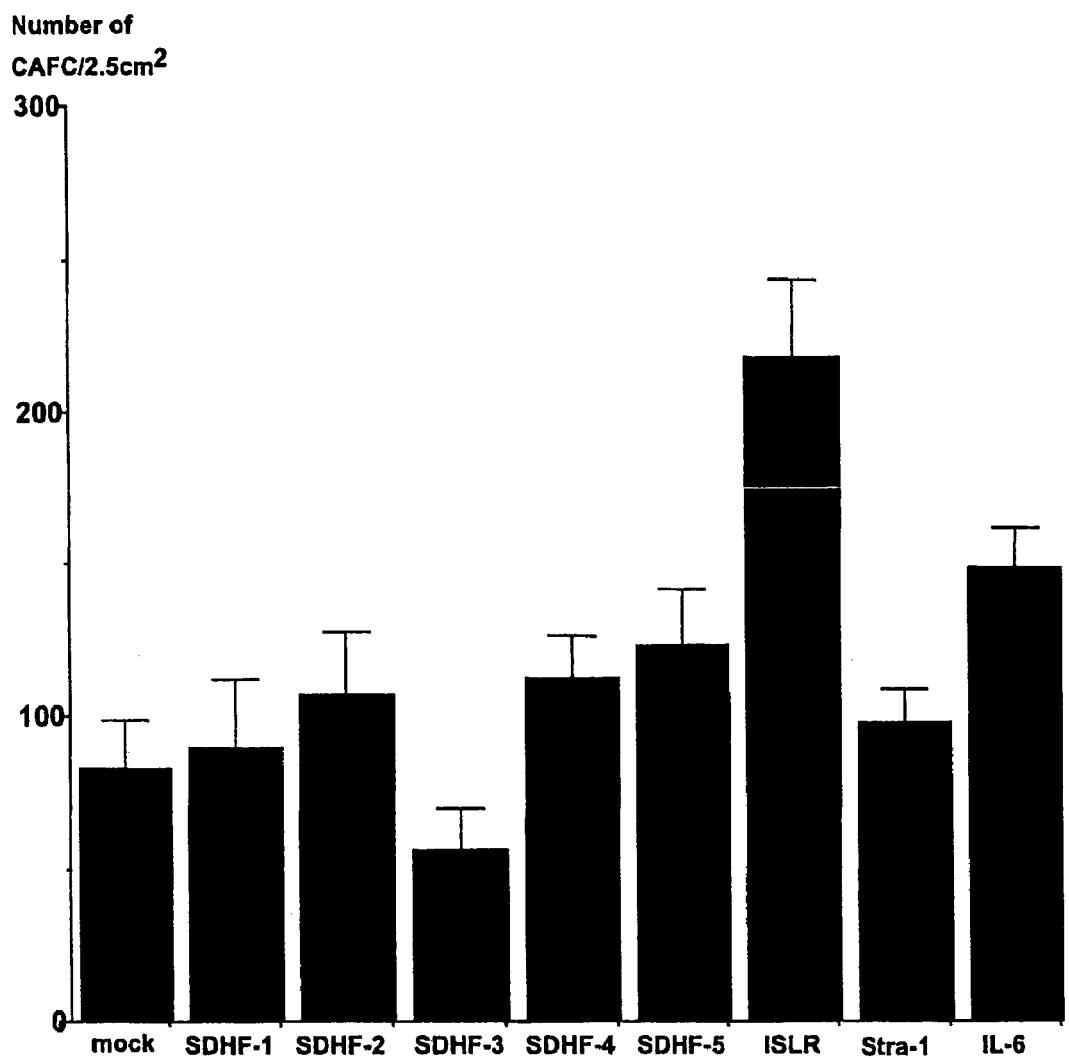
FIG. 11 shows the results of a CAFC analysis.

Hematopoietic cells proliferating underneath a stromal cell layer upon co-culturing the stromal cells and the bone marrow cells are referred to as a cobblestone area forming cell (CAFC). An increased number of the CAFCs formed is largely means that the stromal cell amplifies the immature hematopoietic cells. Nevertheless, an increased CAFC does not mean an amplified hematopoietic stem cell in an exact sense, since the cells consisting the CAFC include not only the hematopoietic stem cell but also the cells which have been differentiated once, such as myelocytic, erythroblastic, megakaryocytic and lymphocytic precursor cells. The gene described above was introduced into the OP9 cells of a mouse myelic stromal cell line having a hematopoiesis-supporting ability using a retrovirus vector pMX-puro, and the cells imparted with a drug resistance by 5 μg/ml puromycin was examined for their CAFC-forming ability. As a result, ISLR exhibited the highest level, and slightly higher levels were also exhibited by SDHF-1, SDHF-2, SDHF-4 and SDHF-5, as shown in FIG. 11. These findings suggest the hematopoietic precursor cell-amplifying ability of these genes. On the contrary, SDHF-3 exhibited the inhibition of the CAFC-constituting ability, and was considered to have a hematopoietic stem cell proliferation-inhibiting ability.

Detection of Secretory Protein in Cell Culture Supernatant by Methionine Labeling $1 \times 10^5$ COS-7 cells were inoculated into a 6 cm dish, which was then incubated overnight. The genes were introduced by a FuGene method (Roche). The carboxyl terminal of any of these genes is tagged with a FLAG tag, and a protein expressed can be detected by a western analysis using an anti-FLAG antibody as described above. After incubation for 36 hours, the supernatant was removed, and the cells were washed twice with PBS, combined with 0.5 ml of DMEM (Methionine, Sigma) supplemented with 0.5 mCi [$^{35}$S] methionine (ICN, TRAN-S), and incubated for 4 hours. The cell components were removed from the culture supernatant by centrifugation, and the proteins were concentrated using a Micron 10 (Millipore). After running in a 15% SDS-PAGE, the labeled proteins were detected using a BAS2000 (FUJI FILM).

Figure 12:
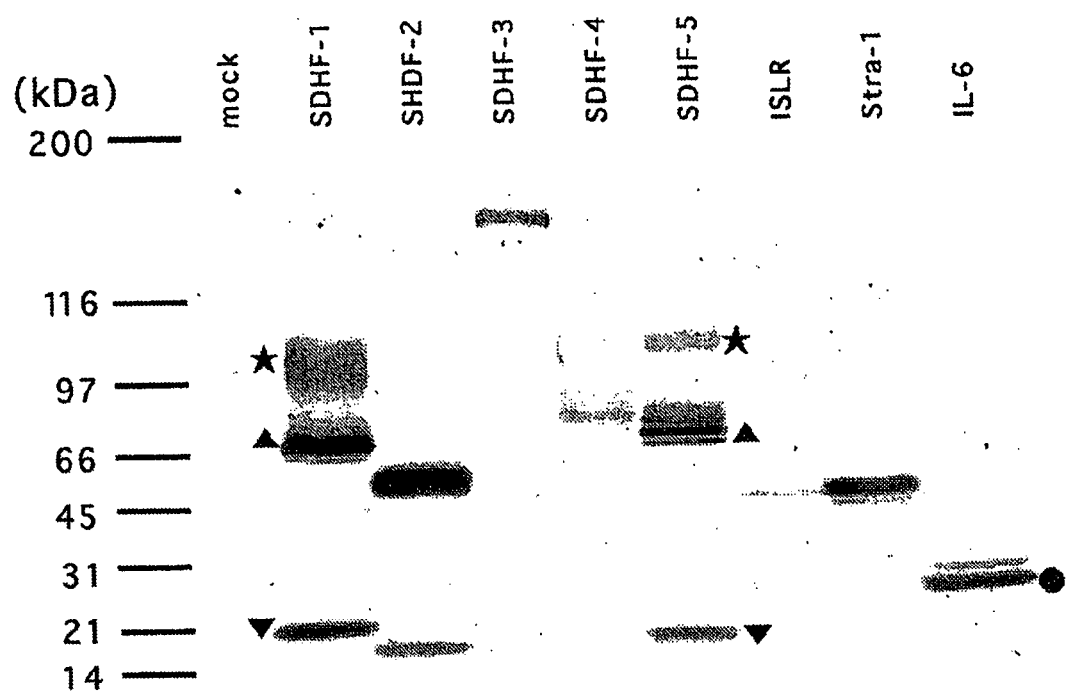
FIG. 12 shows the results of the post-translational modification of the proteins of genes SDHF-1 and SDHF-5 of the invention detected by the western analysis. The symbol "★" indicates a mature protein whose molecular weight became larger as a result of the addition of a sugar chain, the symbol "▲" indicates a protein on the way of the production before the addition of the sugar chain, the symbol "▼" indicates a residual protein after a cleavage, and the symbol "●" indicates a secretory protein.
Figure 13:
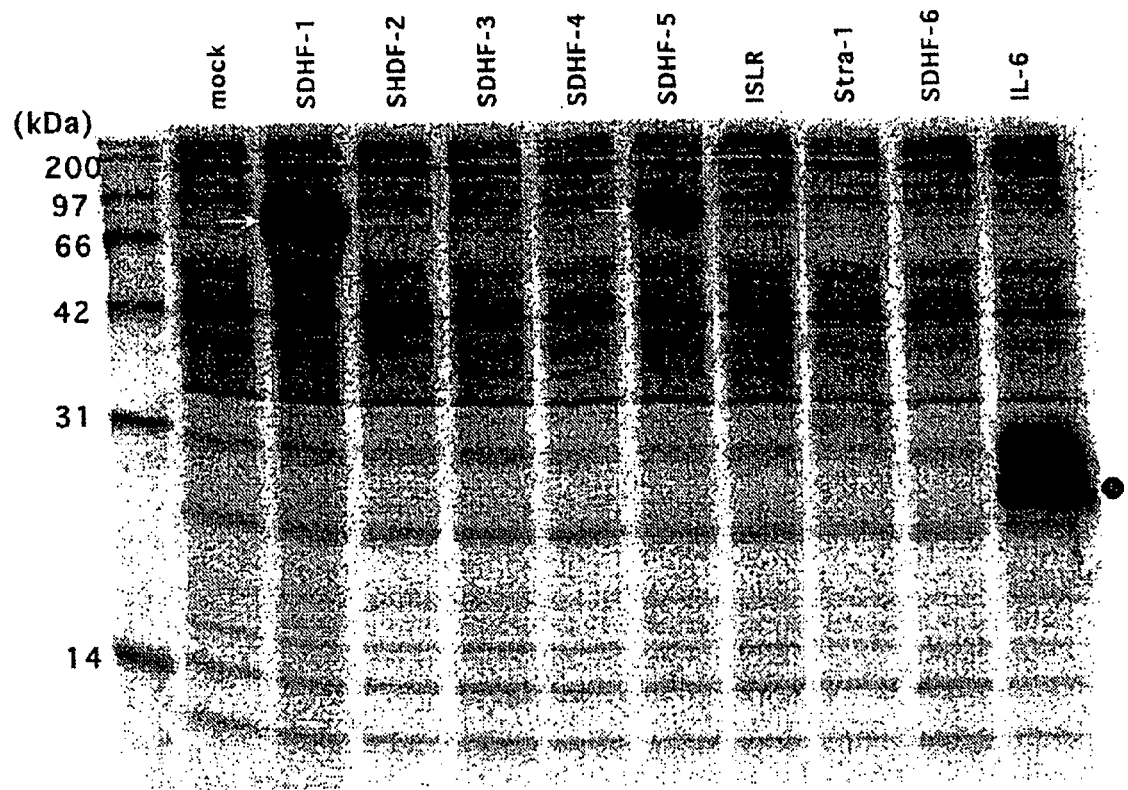
FIG. 13 shows the results of the detection by the methionine labeling of a secretory protein in a cell culture supernatant. The symbol "●" indicates a secretory protein, and "→" indicates a protein secreted in the culture supernatant after a cleavage.

As a result, SDHF-1 and SDHF-5 exhibited the protein secretion to the culture supernatant as shown in FIG. 12 and FIG. 13. Since these genes are membrane proteins structurally and the secretory proteins are smaller by about 20 kDa than the mature protein detected by the western analysis, these secretory proteins were considered to have undergone the cleavage of the transmembrane region of the carboxyl terminals. Since an SCF is known to be a proliferation factor of the type which is secreted as a result of the cleavage of the transmembrane region of the carboxyl terminal and such findings were not shown by an adhesion protein, the proteins encoded by the genes of the invention are suggested strongly to be the proteins of the type which serve as humoral factors to transmit the signals to other cells.

Assay of Expression Site by RT-PCR

Based on the DNA sequences of respective SDHF genes, the primers were designed and a PCR (LA-Tag, TAKARA) was conducted using Multiple Tissue cDNA (MTC) panels (Clontech) as templates. The cells in a bone marrow were sorted by a FACS Vantage (Becton Dickinson) using fluorescence-labeled monoclonal antibodies (anti-B220, anti-CD3, anti-Gr1, anti-MAC1, anti-Sca1 antibodies, Phamingen), subjected to an RNA extraction with a Trizol reagent (Invitrogen) followed by an RT reaction using random hexamers, and then subjected to the PCR similarly.

Figure 14:
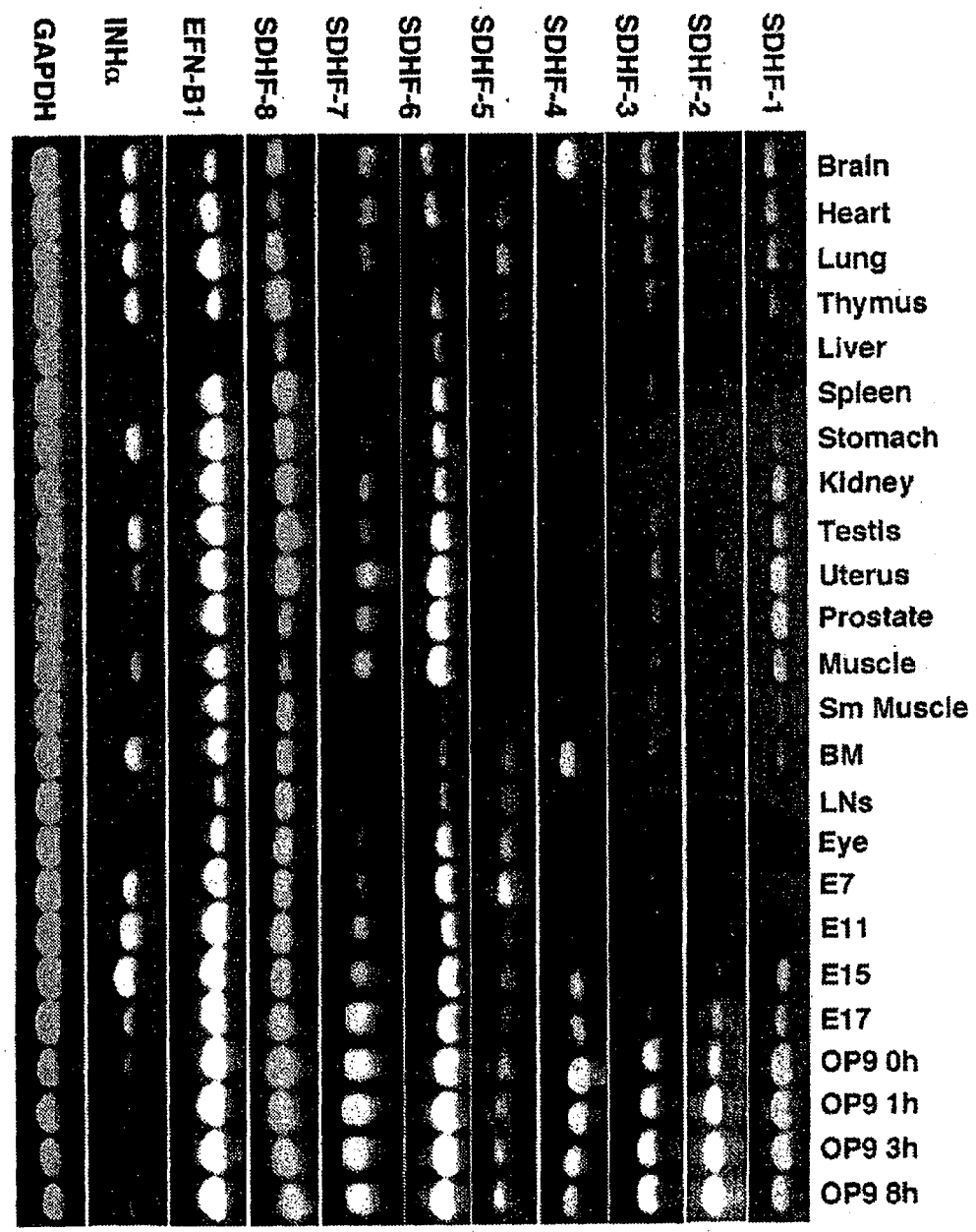
FIGS. 14a, 14b, and 14c show photographs of the electrophoresis showing the results of the assay of the expression site of a gene of the invention by an RT-PCR method.

As a result, all SDHF genes exhibited the expression in the OP9 cells as shown in FIG. 14. SDHF-4 exhibited the expression localized especially in the brain and the bone marrow, in which the expression was localized in the stromal cells interestingly.

Assay of Stem Cell-Supporting Ability by Long Term Culture-Initiating Cells Assay (LTC-IC Method)

Since the CAFC method described above only reflects the hematopoiesis-supporting function over a relatively short period, an LTC-IC method was conducted for the evaluation of the stem cell-supporting function over a prolonged period. A gene isolated as described above was expressed highly in the OP9 cells using a retrovirus expression vector pMX-puro whereby conducting an LTC-IC method.

First, a hematopoietic stem cell was purified. Thus, the bone marrow cells were obtained from the femoral bones of 6 to 8-week old C57BL/6 mice, and the mononuclear cell were separated by centrifugation by a Ficoll method (specific gravity: 1.100). After washing with PBS, the cells were reacted with a biotin-labeled primary antibody (anti-Lineage antibody cocktail: anti-CD3, anti-CD4, anti-CD8, anti-B220, anti-Ter119, anti-Gr1, anti-Mac1 antibodies, all from Phamingen) followed by streptoavidin-labeled magnetic beads each at 4° C. for 15 minutes. A MACS method was employed to recover the column-passing fraction (LIN(−) cells), which was washed by centrifugation, reacted further with a PE-labeled anti-Sca1 antibody, FITC-labeled anti-c-kit antibody, Per-CP-Cy5.5-labeled streptoavidin (all from Phamingen) at 4° C. for 15 minutes, subjected to a FACS Vantage (Becton Dickinson) to obtain LIN (−), Sca1 (+) and c-kit (+) fractions (the cells thus obtained were defined as KSL cells). cDNAs obtained by adding FLAG peptides to the carboxyl terminals of SDHF-1 to 6 were transduced to the OP9 cells using a retrovirus vector (pMX-puro) to establish stably expressing cell lines, 2.5×10⁵ of which were inoculated to a 6-well dish, which were incubated overnight, inoculated with 100 KSL cells, which were then incubated for 3 weeks. Thereafter, the cells were recovered and inoculated, after 2-fold dilution in 8-well pairs, to a 96-well dish, each well of which had been inoculated with 3000 OP9 cells which had been irradiated with γ-ray at 20 Gy. After 5 weeks, the cells were recovered from each well, inoculated to a methyl cellulose medium (IMDM, 1% methyl cellulose, 15% fetal bovine serum, 1% bovine serum albumin, 3 U/ml human erythropoietin, 10 ng/ml human IL-6, 10 ng/ml mouse IL-3, 100 ng/ml mouse SCF, 10 μg/ml bovine insulin), and then evaluated after 12 days on the basis of the presence or absence of the blood cell colonies (CFU-C). The frequency of the stem cells were analyzed by an L-Calc software (Stemcell).

Figure 15:
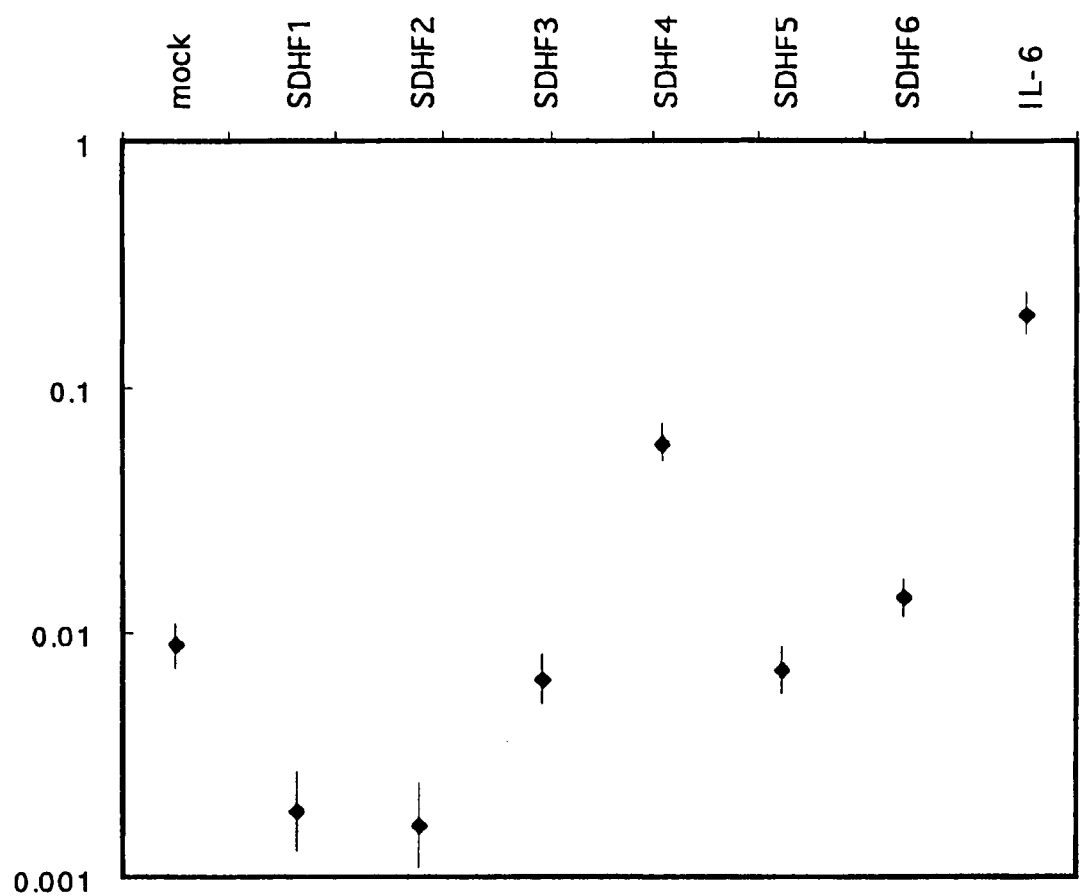
FIG. 15 shows the results of an assay of the stem cell-supporting function of a gene of the invention by an LTC-IC method.

As a result, a marked hematopoiesis-supporting function was exhibited by the SDHF-4 gene as evident from FIG. 15. The hematopoiesis-supporting function of this gene was revealed.

Figure 16:
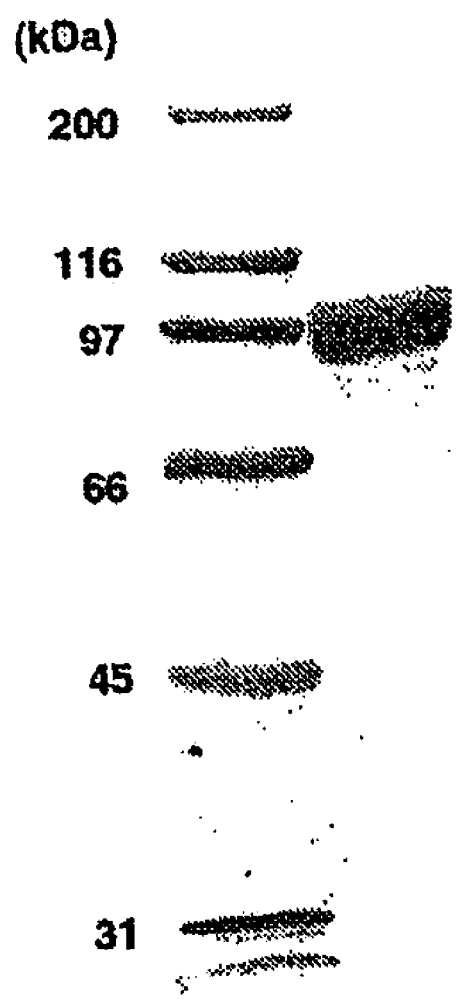
FIG. 16 shows a photograph of the electrophoresis of an SDHF-4 extracellular region/recombinant protein as being purified by a protein A column.
Figure 17:
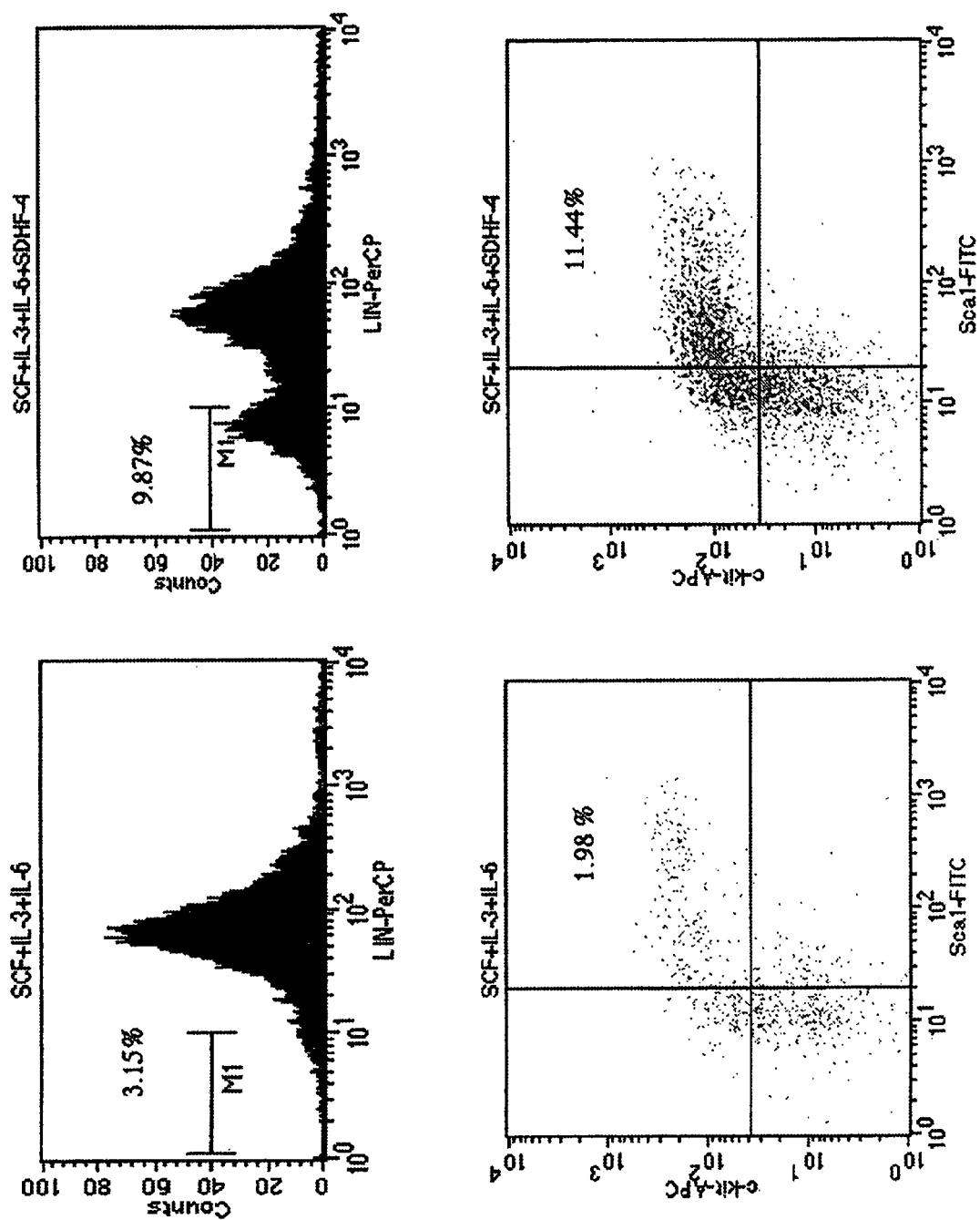
FIG. 17 is a graph showing that the SDHF-4 extracellular region/recombinant protein has an ability of maintaining the non-differentiated condition of a mouse hematopoietic stem cell.
Figure 18:
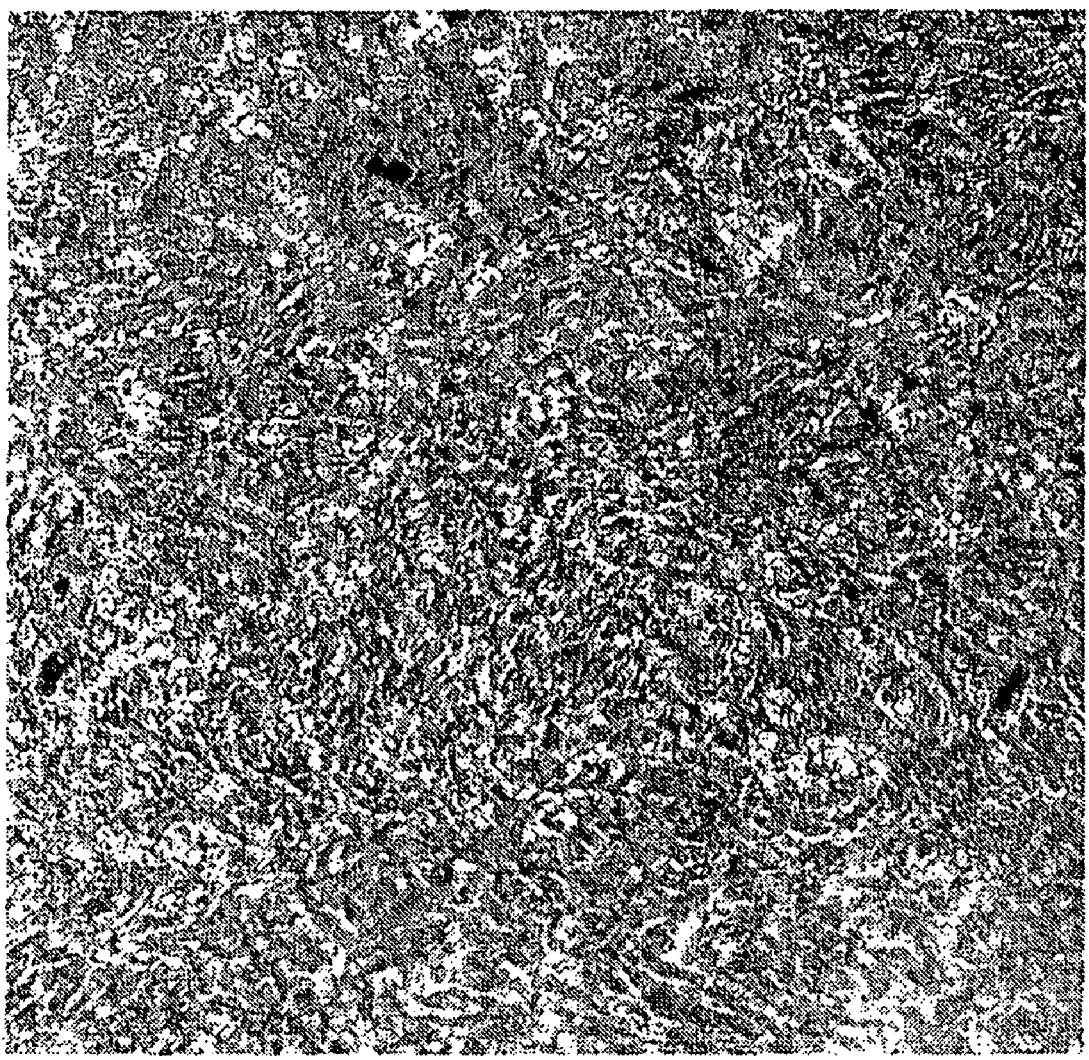
FIG. 18 shows a microscopic photograph (magnification: ×40) showing that SDHF-6, when expressed highly in an OP9 cell using a retrovirus expression vector pMX-puro, has an ability of inducing the differentiation into a fat cell efficiently after about four-week culture.

Mouse Hematopoietic Stem Cell-Amplifying Effect of SDHF-4 Extracellular Region/Recombinant Protein The extracellular transmembrane region of SDHF-4 was assumed (amino acids 524 to 540) using a PSORT II program (http://psort.ims.u-tokyo.ac.jp/form2.html), and a human immunogloblin Fc region and a fusion protein (SDHF-4-Δ TM-Fc) were formed in the extracellular region (amino acids 1 to 523), and subcloned into an expression vector pSSRα, which were stably introduced into CHO-k1 cells. A culture in a serum-free medium CD-CHO (Invitrogen) followed by the purification of the supernatant on a Protein A column yielded fusion recombinant proteins (FIG. 16). Mouse stem cells were cultured similarly to the LTC-IC method as the mouse bone marrow LIN (−), Sca1 (+) and c-kit (+) fractions (KSL cells), each 100 cells of which were incubated in a Stem Span medium (StemCell) supplemented with SCF (50 ng/ml), IL-3 (10 ng/ml), IL-6 (10 ng/ml) and SDHF-4-Δ TM-Fc (100 ng/ml). After 7 days, the cells were recovered, and examined for the expression of LIN, Sca1 and c-kit using a FACS Calibur.

As a result, the LSK cells incubated in the StemSpan medium supplemented with SCF, IL-3 and IL-6 exhibited not only a LIN (−) cell ratio which was higher in the presence rather than the absence of 100 ng/ml of SDHF-4-Δ TM-Fc but also increased ratios of LIN (−), Sca1 (+) and c-kit (+) fractions. These findings suggest that the SDHF-4 extracellular region/recombinant protein has an ability of maintaining the non-differentiated state of the mouse hematopoietic stem cells.

Fat Cell Differentiation Assay and Oil Red O Staining

Each of the cell into which an SDHF-6 gene had been transduced via a retrovirus vector (pMX-puro) and the cell into which only the vector had been transduced was incubated continuously in a confluent state without any subculture over a period of 4 weeks or longer in the presence of Alpha-MEM+20% fetal bovine serum. The cells were fixed with 10% formalin and then stained with an Oil Red 0.

As a result, the OP9 cells over expressing SDHF-6 by using the retroviral vector pMX-puro were revealed to differentiate into fat cells with a high efficiency after the incubation for about 4 weeks. This gene was considered to be involved in the differentiation into the fat cells via the effect on the mesencymal cells rather than on the hematopoietic stem cells.

Preparation of Polyclonal Antibody Directed to SDHF-4 and Isolation of myelic Hematopoiesis-Supporting Cell Therewith Based on the amino acid sequence of SDHF-4, a synthetic peptide (GYMAKDKFRRMNEGQVY (SEQ ID NO: 14) (corresponding to the amino acids 32 to 48)) was designed, and immunized to a rabbit to prepare a polyclonal antibody.

Figure 19:
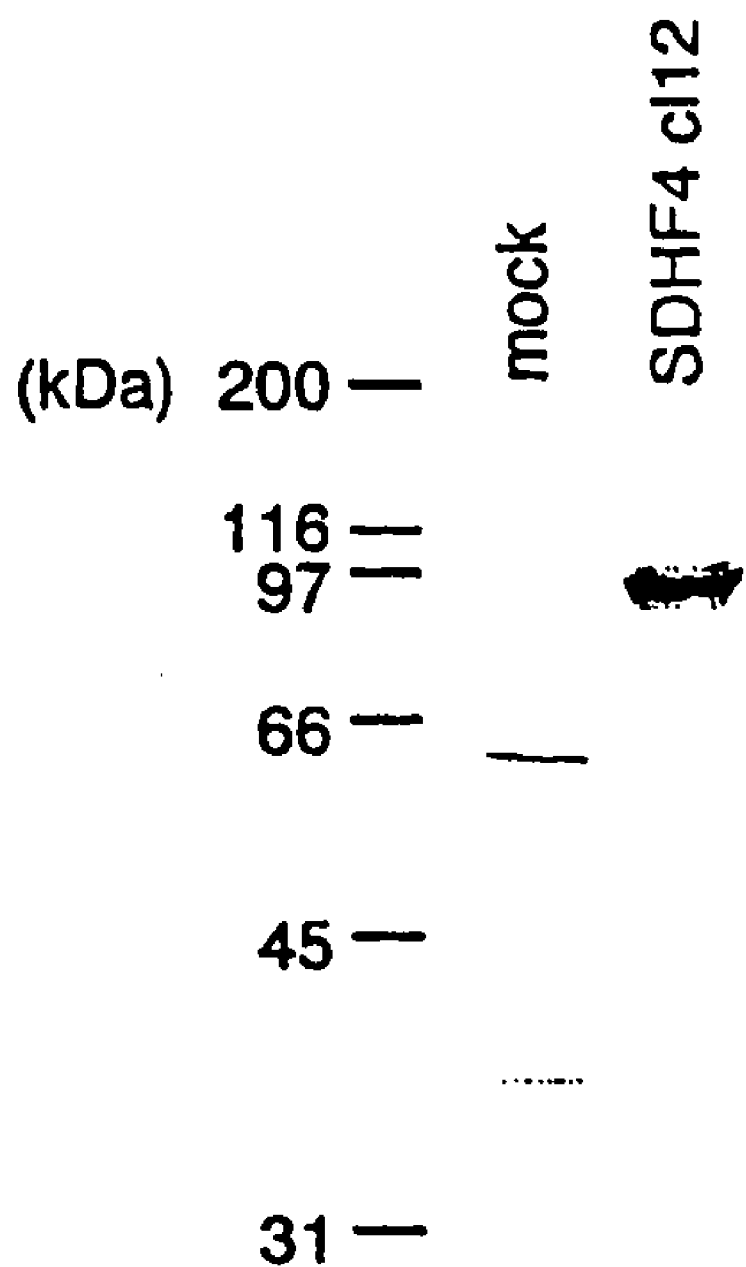
FIG. 19 shows a photograph of a western analysis showing the results of the experiment in which an antibody directed to a partial peptide of SDHF-4 was employed to allow SDHF-4 to be expressed in a CHO-k1 cell using a pSSRα-bsr vector.
Figure 22:
FIG. 22 shows a microscopic photograph of the above-mentioned cell selected by the sorting (magnification: ×200).
Figure 23:
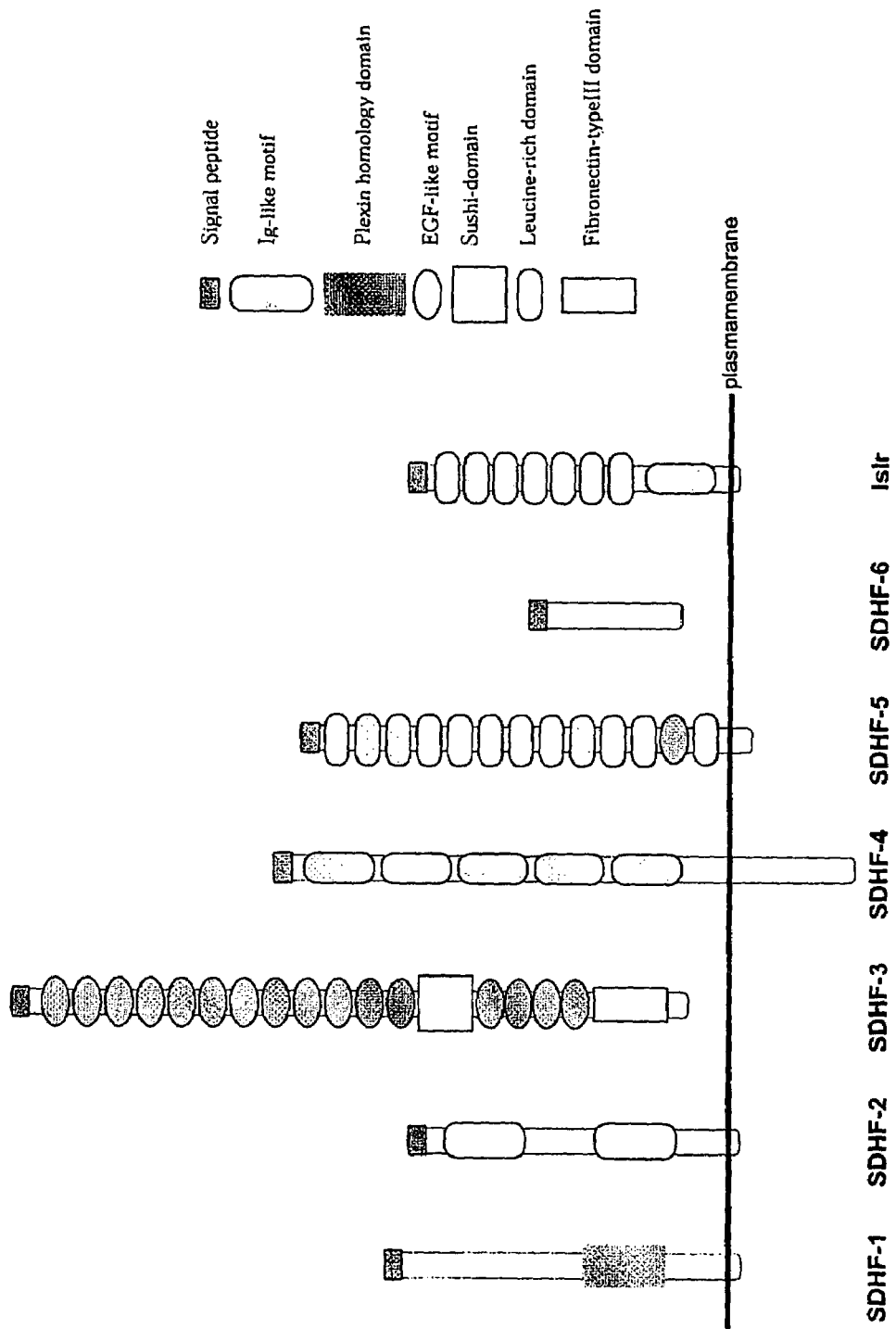
FIG. 23 shows a schematic view of the molecular structures of SDHF-1 to SDHF-6.

This peptide was conjugatal with an epoxy-activated agarose gel SEPHAROSE 6B) (Pharmacia) to prepare an antigen column, which was used to purificate a polyclonal antibody, as an affinity chromatography. A western analysis using this antibody while comparing the cell expressing SDHF-4 obtained by transducing a CHO-k1 cell with a pSSRα-bsr vector (SDHF4-c112) with the cell into which only the vector had been introduced (mock) revealed that an SDHF-4 gene product could be recognized in a very specific manner (FIG. 19). 1 mg of the resultant purified antibody was labeled with FITC using a LinKit Fluoro-Link (ISL) and the same cell was analyzed by a FACS Calibur (Becton Dickinson), and the results indicated that this antibody can be utilized also in a flow cytometry (FIG. 20: O-line: mock, ■-line: SDHF4-c112). Using this antibody, the bone marrow cells of a C57BL/6J mouse were stained, and subjected to a FAGS Vantage (Becton Dickinson) whereby sorting and recovering the cells expressing SDHF-4 (FIG. 21), which deposited onto a culture dish and were revealed morphologically to be mesencymal cells corresponding to bone marrow hematopoiesis-supporting cells (FIG. 22).

INDUSTRIAL APPLICABILITY

According to the invention, a stromal cell-derived novel hematopoiesis-related gene can be isolated successfully, and was revealed to have a hematopoietic stem cell proliferation-regulating activity. As a result, a wide range of the application, including an in vitro amplification of hematopoietic stem cells, a transplantation therapy against a malignant tumor of a hematopoietic tissue, a regenerative medicine using the stem cell, a gene therapy, immunotherapy, cell transplantation, treatments of a neuropathy (Alzheimer's disease, cerebral infarction, degenerative neuropathy and the like), hepatic disease (cirrhosis), pulmonary disease, myocardial disease, diabetes, bone disease, chronic renal failure and the like, became possible.

What is claimed is:

1. A gene encoding a protein comprising an amino acid sequence represented by SEQ ID No. 8.

2. A gene comprising a DNA consisting of the base sequence represented by SEQ ID No.7.

3. A protein encoded by a gene according to claim 1 or 2.

4. A recombinant expression vehicle comprising at least one gene according to claim 1 or 2.

5. A recombinant expression vehicle according to claim 4 which is a recombinant plasmid vector.

6. A recombinant expression vehicle according to claim 4 which is a recombinant retrovirus vector.

7. A transformant obtained by a transformation by an expression vehicle according to claim 4.

8. A transformant according to claim 7 which is a COS-7 cell.

9. A transformant according to claim 7 which is a stromal cell.

10. A method for producing a protein comprising culturing a transformant according to claim 7.

* * * * *